United States Patent
McKay et al.

(10) Patent No.: US 8,470,354 B2
(45) Date of Patent: Jun. 25, 2013

(54) OSTEOGENIC IMPLANTS WITH COMBINED IMPLANT MATERIALS AND METHODS FOR SAME

(75) Inventors: William F. McKay, Memphis, TN (US); Scott D. Boden, Atlanta, GA (US); Neil B. Beals, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 161 days.

(21) Appl. No.: 12/684,480

(22) Filed: Jan. 8, 2010

(65) Prior Publication Data

US 2010/0266660 A1   Oct. 21, 2010

Related U.S. Application Data

(60) Division of application No. 11/361,026, filed on Feb. 23, 2006, now Pat. No. 7,722,895, which is a continuation of application No. 11/118,124, filed on Apr. 29, 2005, now abandoned.

(60) Provisional application No. 60/611,527, filed on Sep. 20, 2004.

(51) Int. Cl.
  *A61F 2/00* (2006.01)
  *A61F 2/02* (2006.01)
  *A61F 2/28* (2006.01)
  *A61K 38/00* (2006.01)
  *A61K 38/16* (2006.01)
  *A61K 38/17* (2006.01)
  *A61K 38/18* (2006.01)
  *C07K 14/78* (2006.01)
  *C07K 14/51* (2006.01)

(52) U.S. Cl.
  USPC ............ 424/423; 514/1.1; 514/801; 424/422; 523/115; 106/160.1; 435/273; 530/356; 606/229

(58) Field of Classification Search
  None
  See application file for complete search history.

(56) References Cited

U.S. PATENT DOCUMENTS 4,394,370 A   7/1983   Jefferies
4,516,276 A   5/1985   Mittelmeier et al.
(Continued)

FOREIGN PATENT DOCUMENTS

EP   0309241   3/1989
EP   0530804   3/1993
(Continued)

OTHER PUBLICATIONS

Akamaru, Tomoyuki et al., Simple Carrier Matrix Modifications Can Enhance Deliery of Recombinant Human Bone Morphogenetic Protein-2 for Posterolateral Spine Fusion, SPINE, vol. 28, No. 5, pp. 429-434, 2003.

(Continued)

*Primary Examiner* — Elizabeth C Kemmerer
(74) *Attorney, Agent, or Firm* — Sorell Lenna & Schmidt LLP

(57) ABSTRACT

Described are osteogenic implants that include a first implant material covered at least in part by a second implant material carrying an osteogenic protein such as a bone morphogenic protein. The first implant material can comprise a mineral and provide an inner scaffolding portion for supporting bone ingrowth, and the second implant material can comprise a collagen or other sponge carrier covering the first implant material and having a liquid osteogenic protein formulation imbibed therein. Related implant materials and methods of preparation and use constitute additional aspects of the invention.

16 Claims, 3 Drawing Sheets

U.S. PATENT DOCUMENTS

| | | | |
|---|---|---|---|
| 4,743,229 A | 5/1988 | Chu | |
| 4,755,184 A | 7/1988 | Silverberg | |
| 4,776,890 A | 10/1988 | Chu | |
| 4,780,450 A | 10/1988 | Sauk et al. | |
| 4,865,602 A | 9/1989 | Smestad et al. | |
| 4,888,366 A | 12/1989 | Chu et al. | |
| 4,992,226 A | 2/1991 | Piez et al. | |
| 5,001,169 A | 3/1991 | Nathan et al. | |
| 5,002,583 A | 3/1991 | Pitaru et al. | |
| 5,035,715 A | 7/1991 | Smestad et al. | |
| 5,123,925 A | 6/1992 | Smestad et al. | |
| 5,231,169 A | 7/1993 | Constantz et al. | |
| 5,246,457 A | 9/1993 | Piez et al. | |
| 5,273,964 A | 12/1993 | Lemons | |
| 5,425,770 A | 6/1995 | Piez et al. | |
| 5,573,771 A | 11/1996 | Geistlich et al. | |
| 5,702,449 A | 12/1997 | McKay | |
| 5,776,193 A | 7/1998 | Kwan et al. | |
| 5,785,710 A | 7/1998 | Michelson | |
| 6,905,516 B1 * | 6/2005 | Lemaitre et al. | 623/23.56 |
| 2002/0082694 A1 | 6/2002 | McKay | |
| 2005/0042253 A1 | 2/2005 | Farrar et al. | |
| 2005/0169893 A1 | 8/2005 | Koblish et al. | |
| 2005/0169956 A1 | 8/2005 | Erbe et al. | |
| 2005/0214340 A1 | 9/2005 | Erbe et al. | |

FOREIGN PATENT DOCUMENTS

| | | |
|---|---|---|
| EP | 0747067 | 12/1996 |
| WO | WO 89/04646 | 6/1989 |
| WO | WO 96/39203 | 12/1996 |
| WO | WO 97/31661 | 9/1997 |
| WO | WO 97/40137 | 10/1997 |
| WO | WO 98/17330 | 4/1998 |
| WO | WO 00/71178 A1 * | 11/2000 |

OTHER PUBLICATIONS

Alam, Md. Imranul et al., Evaluation of ceramics composed of different hydroxyapatite to tricalcium phosphate ratios as carriers for rhBMP-2, Biomaterials 22 (2001), pp. 1643-1651.

Albee, Fred H., Studies in Bone Growth: Triple Calcium Phosphate as a Stimulus to Osteogenesis, Ann Surg. Jan. 1920;71(1):32-9.

Banwart, J. Christopher et al., Iliac Crest Bone Graft Harvest Donor Site Morbidity, a Statistical Evaluation, SPINE, vol. 20, No. 9, pp. 1055-1060, 1995.

Boden, Scott D. et al., Laparoscopic Anterior Spinal Arthrodesis with rhBMP-2 in a titanium Interbody Threaded Cage, J. of Spinal Disorders, vol. 11, No. 2, pp. 95-101, 1998.

Boden, Scott D. et al., Posterolateral Lumbar Intertransverse Process Spine Arthrodesis With Recombinant Human Bone Morphogenetic Protein 2/Hydroxyapatite-Tricalcium Phosphate After Laminectyomy in the Nonhuman Primate, SPINE, vol. 24, No. 12, pp. 1179-1185, 1999.

Boden, Scott D. et al., Video-Assisted Lateral Intertransverse Process Arthrodesis, Spine, vol. 21, No. 22, pp. 2689-2697, 1996.

Boden, Scott D., et al., Use of Recombinant Human Bone Morphogenetic Protein-2 to Achieve Posterolateral Lumbar Spine Fusion in Humans, SPINE, vol. 27, No. 23, pp. 2662-2673, 2002.

Boden, Scott, Overview of the Biology of Lumbar Spine Fusion and Principles for Selecting a Bone Graft Substitute, SPINE, vol. 27, No. 16S, pp. S26-S31, 2002.

Burkus, J. Kenneth et al., Anterior Lumbar Interbody Fusion Using rhBMP-2 With Tapered Interbody Cages, J. Spinal Disorders & Techniques, vol. 15, No. 5, pp. 337-349, 2002.

Burkus, J. Kenneth et al., Clinical and Radiographic Outsomes of Anterior Lumbar Interbody Fusion Using Recombinant Human Bone Morphogenetic Protein-2, SPINE, vol. 27, No. 21, pp. 2396-2408, 2002.

Burkus, J. Kenneth et al., Is INFUSE Bone Graft Superior to Autograft Bone? An Integrated Analysis of Clinical Trials Using the LT-CAGE Lumbar Tapered Fusion Device, J. Spinal Disorders & Techniques, vol. 16, No. 2, pp. 113-122, 2003.

Burkus, J. Kenneth et al., Radiographic Assessment of Interbody Fusion Using Recombinant Human Bone Morphogenetic Protein, SPINE, vol. 28, No. 4, pp. 372-377, 2003.

Canady, John W. et al., Suitability of the iliac Crest as a Site for Harvest of Autogenous Bone Grafts, Cleft Palate Craniofac J. Nov. 1993; 30(6):579-81.

Daculsi, G., Biphasic calcium phosphate concept applied to artificial bone, implant coating and injectable bone substitute, Bomaterials 19 (1998), pp. 1473-1478.

Damien, Christopher J., Bone Graft and Bone Graft Substitutes: A Review of Current Technology and Applications, J. Applied Biomaterials, vol. 2, pp. 187-208, 1991.

David, Stephen M. et al., Lumbar Spinal Fusion Using Recombinant Human Bone Morphogenetic Protein in the Canine, SPINE, vol. 24, No. 19, pp. 1973-1979, 1999.

Fujibayashi, Shunsuke et al., Lumbar Posterolateral Fusion with Biphasic Calcium Phospate Ceramic, J Spinal Disorders, vol. 14, No. 3, pp. 214-221, 2001.

Glassman, Steven D., et al., Posterolateral lumbar spine fusion with INFUSE bone graft, The Spine Journal 7 (2007) 44-49.

Hacker, Robert J., A randomized prospective study of an anterior cervical interbody fusion device with a minimum of 2 years of follow-up results, J. Neurosurg (Spine 2) 93:222-226, 2000.

Haid, Regis W. Jr., et al., Posterior lumbar interbody fusion using recombinant human bone morphogenetic protein type 2 with cylindrical interbody cages, The Spine Hournal 4 (2004), pp. 527-539.

Heary, Robert F. et al., Persistent Iliac Crest Donor Site Pain: Independent Outcome Assessment, Neurosurgery, vol. 50, No. 3, Mar. 2002.

Hecht, Brian P. et al., The Use of Recombinant Human Bone Morphogenetic Protein 2 (rhBMP-2) to Promote Spinal Fusion in a Nonhuman Primate Anterior Interbody Fusion Model, SPINE, vol. 24, No. 7, pp. 629-636, 1999.

Heise, U. et al., Hydroxyapatite ceramic as a bone substitute, International Orthopaedics, (SICOT) 14:329-338, 1990.

Hollinger, Jeffrey O. et al, Role of Bone Substitutes, Clincial Orthopaedics and Related Research, No. 324, pp. 55-56, 1996.

Jarcho, M., Calcium phosphate ceramics as hard tissue prosthetics, Clin Orthop Relat Res. Jun. 1981;(157):259-78.

Kraiwattanapong, Chaiwat et al., Comparision of Healos/Bone Marrow to INFUSE (rhBMP-2/ACS) With a Collagen-Ceramic Sponge Bulking Agent as Grit Substitutes for Lumbar Spine Fusion, SPINE, vol. 30, No. 9, pp. 1001-1007, 2005.

Kurz, Lawrence T. et al., Harvesting Autogenous Iliac Bone Grafts, SPINE, vol. 14, No. 12, pp. 1324-133, 1989.

Laurie, Simon W.S. et al., Donor-Site Morbidity after Harvesting Rib and Iliac Bone, Plastic and Reconstructive Surgery, vol. 73, No. 6, pp. 993-938, 1984.

Lehmann, Thomas R. et al., Abstract, Incidence of Chronic Donor Site Pain from Posterior Iliac Bone Harvesting, International Society for the Study of the Lumbar Spine, 29th Annual Meeting, May 14-18, 2002.

Martin, George J., Posterolateral Intel-transverse Process Spinal Arthrodesis with rhBMP-2 in a Nonhuman Primate: Important Lessons Learned Regarding Dose, Carrier, and Safety, J. Spinal Disorders, vol. 12, No. 3, pp. 179-186, 1999.

McKay, Bill, Use of Recominant Human Bone Morphogenetic Protein-2 in Spinal Fusion Applications, SPINE, vol. 27, No. 16 Supp, pp. S66-S85, Aug. 2002.

Metsger, Scott et al., Tricalcium phosphate ceramic—A resorbable bone implant review and current status, JADA, vol. 105, pp. 1035-1038, 1982.

Minamide et al., Use of rhBMP-2 Supplemented with Allograft Bone Chips in Posterolateral Fusions in Non-Human Primates, North American Spine Society 2001, Atlanta, Georgia.

Minamide, A. et al., Use of rhBMP-2 Supplemented with Allograft Bone Chips in Posterolateral Fusions in Non-Human Primates, North American Society 16th Annual Meeting, Oct. 31-Nov. 3, 2001 in Seattle Washington, 2001.

Minamide, Akihito et al., Evaluation of Carriers of Bone Morphogenetic Protein for Spinal Fusion, SPINE, vol. 26, No. 8, pp. 933-939, 2001.

Nakamura, Konishi S. et al., Hydroxyapatite granule graft combined with recombinant human bone morphogenic protein-2 for solid lumbar fusion, J. Spinal Disord Tech Jun. 2002; 15(3):237-44.

Passuti, N. et al., Macroporous Calcium Phosphate Ceramic Performance in Human Spine Fusion, Clinical Orthopaedics and Related Research, No. 248, pp. 169-176, 1989.

Powerpoint Slide Presentation, Boden, S.D. et al. Comparisonof Healos/Bone Marrow to INFUSE (rhMBP-2) as Graft Substitutes for Lumbar Spine Fusion, Bone Summit 2003, Maastricht, Netherlands, Oct. 11, 2003.

Powerpoint slide presentation, Boden, S.D. et al., Comparison of Healos/Bone Marrow to INFUSE (rhBMP-2) as Graft Substitutes for Lumbar Spine Fusion, Bone Summit 2004, Cleveland, Ohio, May 15, 2004.

Poynton, Ashley et al., Safety Profile for the Clinical Use of Bone Morpohgenetic Proteins in the Spine, SPINE, vol. 27, No. 16S, pp. S40-S48, 2002.

Ransford, A.O. et al., Synthetic porous ceramic compared with autograft in scoliosis surgery, J. Bone & Joint Surgery, vol. 80-B, No. 1, pp. 13-18, 1998.

Sandhu, Harvinder S. et al., Effective Doses of Recombinant Human Bone Morphogenetic Protein-2 in Experimental Fusion, SPINE, vol. 21, No. 18, pp. 2115-2122, 1996.

Sandhu, Harvinder S. et al., Experimental Spinal Fusion with Recombinant Human Bone Morphogenetic Protein-2 Without Decortication of Osseous Elements, SPINE, vol. 22, No. 11, pp. 117-1180, 1997.

Sandhu, Harvinder, Bone Morphogenetic Proteins and spinal Surgery, SPINE, vol. 28, No. 15S, pp. S64-S73, 2003.

Sawin, Paul D. et al., A comparative analysis of fusion rates and donor-site morbidity for autogeneic rib and iliac crest bone grafts in postrior cervical fusions, J. Neurosurg 88, pp. 255-265, 1998.

Schimandle, Jeffrey H. et al., Experimental Spinal Fusion With Recombinant Human Bone Morphogenetic Protein-2, SPINE, vol. 20, No. 12, pp. 1326-1337, 1995.

Slide Presentation, Optimized Carrier Matrix Allows Lower Dose of rhBMP-2 to Achieve spine Fusion, A Study in Non-Human Primates, 18th Annual Meeting of the North American Spine Society, Oct. 23, 2003.

St. John, T.A. et al., Physical and monetary costs associated with autogenous bone graft harvesting, Am. J. Orthop. Jan. 2003; 32(1):18-23.

Wang, J.C. et al., rhBMP-2 Repairs Pseudarthrosis After Posterolateral Fusion, 47th Annual Meeting, Orthopaedic Research Society, Feb. 25-28, 2001, San Francisco, CA.

Wang, Jianxin, Biological evaluation of biphasic calcium phosphate ceramic vertebral alminae, Biomaterials 19 (1998), pp. 1387-1392.

U.S. Appl. No. 11/361,026, filed Feb. 23, 2006.

* cited by examiner

SEQUENCE LISTING

```
<160> NUMBER OF SEQ ID NOS: 8

<210> SEQ ID NO 1
<211> LENGTH: 1547
<212> TYPE: DNA
<213> ORGANISM: Homo sapiens
<220> FEATURE:
<221> NAME/KEY: CDS
<222> LOCATION: (324)..(1514)

<400> SEQUENCE: 1
ggggacttct tgaacttgca gggagaataa cttgcgcacc ccactttgcg ccggtgcctt      60
tgccccagcg gagcctgctt cgccatctcc gagcccacc gcccctccac tcctcggcct     120
tgcccgacac tgagacgctg ttcccagcgt gaaaagagag actgcgcggc cggcacccgg    180
gagaaggagg aggcaaagaa aaggaacgga cattcggtcc ttgcgccagg tcctttgacc    240 agagttttc catgtggacg ctctttcaat ggacgtgtcc ccgcgtgctt cttagacgga    300
ctgcggtctc ctaaaggtcg acc atg gtg gcc ggg acc cgc tgt ctt cta gcg    353
                        Met Val Ala Gly Thr Arg Cys Leu Leu Ala
                         1               5                  10
```

```
ttg ctg ctt ccc cag gtc ctc ctg ggc ggc gcg gct ggc ctc gtt ccg      401
Leu Leu Leu Pro Gln Val Leu Leu Gly Gly Ala Ala Gly Leu Val Pro
            15                  20                  25 gag ctg ggc cgc agg aag ttc gcg gcg gcg tcg tcg ggc cgc ccc tca      449
Glu Leu Gly Arg Arg Lys Phe Ala Ala Ala Ser Ser Gly Arg Pro Ser
        30                  35                  40 tcc cag ccc tct gac gag gtc ctg agc gag ttc gag ttg cgg ctg ctc      497
Ser Gln Pro Ser Asp Glu Val Leu Ser Glu Phe Glu Leu Arg Leu Leu
                45                  50                  55 agc atg ttc ggc ctg aaa cag aga ccc acc ccc agc agg gac gcc gtg      545
Ser Met Phe Gly Leu Lys Gln Arg Pro Thr Pro Ser Arg Asp Ala Val
        60                  65                  70 gtg ccc ccc tac atg cta gac ctg tat cgc agg cac tca ggt cag ccg      593
Val Pro Pro Tyr Met Leu Asp Leu Tyr Arg Arg His Ser Gly Gln Pro
75                  80                  85                  90 ggc tca ccc gcc cca gac cac cgg ttg gag agg gca gcc agc cga gcc      641
Gly Ser Pro Ala Pro Asp His Arg Leu Glu Arg Ala Ala Ser Arg Ala
                95                  100                 105 aac act gtg cgc agc ttc cac cat gaa gaa tct ttg gaa gaa cta cca      689
Asn Thr Val Arg Ser Phe His His Glu Glu Ser Leu Glu Glu Leu Pro
        110                 115                 120 gaa acg agt ggg aaa aca acc cgg aga ttc ttc ttt aat tta agt tct      737
Glu Thr Ser Gly Lys Thr Thr Arg Arg Phe Phe Phe Asn Leu Ser Ser
        125                 130                 135 atc ccc acg gag gag ttt atc acc tca gca gag ctt cag gtt ttc cga      785
Ile Pro Thr Glu Glu Phe Ile Thr Ser Ala Glu Leu Gln Val Phe Arg
        140                 145                 150 gaa cag atg caa gat gct tta gga aac aat agc agt ttc cat cac cga      833
Glu Gln Met Gln Asp Ala Leu Gly Asn Asn Ser Ser Phe His His Arg
155                 160                 165                 170 att aat att tat gaa atc ata aaa cct gca aca gcc aac tcg aaa ttc      881
Ile Asn Ile Tyr Glu Ile Ile Lys Pro Ala Thr Ala Asn Ser Lys Phe
                175                 180                 185 ccc gtg acc aga ctt ttg gac acc agg ttg gtg aat cag aat gca agc      929
Pro Val Thr Arg Leu Leu Asp Thr Arg Leu Val Asn Gln Asn Ala Ser
        190                 195                 200 agg tgg gaa agt ttt gat gtc acc ccc gct gtg atg cgg tgg act gca      977
Arg Trp Glu Ser Phe Asp Val Thr Pro Ala Val Met Arg Trp Thr Ala
        205                 210                 215 cag gga cac gcc aac cat gga ttc gtg gtg gaa gtg gcc cac ttg gag     1025
Gln Gly His Ala Asn His Gly Phe Val Val Glu Val Ala His Leu Glu
        220                 225                 230 gag aaa caa ggt gtc tcc aag aga cat gtt agg ata agc agg tct ttg     1073
Glu Lys Gln Gly Val Ser Lys Arg His Val Arg Ile Ser Arg Ser Leu
235                 240                 245                 250 cac caa gat gaa cac agc tgg tca cag ata agg cca ttg cta gta act     1121
His Gln Asp Glu His Ser Trp Ser Gln Ile Arg Pro Leu Leu Val Thr
                255                 260                 265 ttt ggc cat gat gga aaa ggg cat cct ctc cac aaa aga gaa aaa cgt     1169
Phe Gly His Asp Gly Lys Gly His Pro Leu His Lys Arg Glu Lys Arg
        270                 275                 280 caa gcc aaa cac aaa cag cgg aaa cgc ctt aag tcc agc tgt aag aga     1217
Gln Ala Lys His Lys Gln Arg Lys Arg Leu Lys Ser Ser Cys Lys Arg
        285                 290                 295 cac cct ttg tac gtg gac ttc agt gac gtg ggg tgg aat gac tgg att     1265
His Pro Leu Tyr Val Asp Phe Ser Asp Val Gly Trp Asn Asp Trp Ile
        300                 305                 310 gtg gct ccc ccg ggg tat cac gcc ttt tac tgc cac gga gaa tgc cct     1313
Val Ala Pro Pro Gly Tyr His Ala Phe Tyr Cys His Gly Glu Cys Pro
315                 320                 325                 330
```

```
ttt cct ctg gct gat cat ctg aac tcc act aat cat gcc att gtt cag      1361
Phe Pro Leu Ala Asp His Leu Asn Ser Thr Asn His Ala Ile Val Gln
                335                 340                 345 acg ttg gtc aac tct gtt aac tct aag att cct aag gca tgc tgt gtc      1409
Thr Leu Val Asn Ser Val Asn Ser Lys Ile Pro Lys Ala Cys Cys Val
            350                 355                 360 ccg aca gaa ctc agt gct atc tcg atg ctg tac ctt gac gag aat gaa      1457
Pro Thr Glu Leu Ser Ala Ile Ser Met Leu Tyr Leu Asp Glu Asn Glu
        365                 370                 375 aag gtt gta tta aag aac tat cag gac atg gtt gtg gag ggt tgt ggg      1505
Lys Val Val Leu Lys Asn Tyr Gln Asp Met Val Val Glu Gly Cys Gly
    380                 385                 390 tgt cgc tag tacagcaaaa ttaaatacat aaatatatat ata                    1547
Cys Arg
395

<210> SEQ ID NO 2
<211> LENGTH: 396
<212> TYPE: PRT
<213> ORGANISM: Homo sapiens

<400> SEQUENCE: 2

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270
```

-continued

```
Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
                340                 345                 350

Asn Ser Lys Ile Pro Lys Ala Cys Cys Val Pro Thr Glu Leu Ser Ala
                355                 360                 365

Ile Ser Met Leu Tyr Leu Asp Glu Asn Glu Lys Val Val Leu Lys Asn
            370                 375                 380

Tyr Gln Asp Met Val Val Glu Gly Cys Gly Cys Arg
385                 390                 395

<210> SEQ ID NO 3
<211> LENGTH: 1400
<212> TYPE: DNA
<213> ORGANISM: Homo sapiens
<220> FEATURE:
<221> NAME/KEY: CDS
<222> LOCATION: (102)..(1310)

<400> SEQUENCE: 3
gaggcactgc ttggaagcaa ttgtagagca atacagctct tgacaaactc gtgtcgaaca      60
tcagtgactg ttgaagggaa tgaggcaaac atatctacgg a atg ctg atg gtc gtt    116
                                              Met Leu Met Val Val
                                                1               5 tta tta tgc caa gtc ctg cta gga ggc gcg agc cat gct agt ttg ata      164
Leu Leu Cys Gln Val Leu Leu Gly Gly Ala Ser His Ala Ser Leu Ile
            10                  15                  20 cct gag acg ggg aag aaa aaa gtc gcc gag att cag ggc cac gcg gga      212
Pro Glu Thr Gly Lys Lys Lys Val Ala Glu Ile Gln Gly His Ala Gly
        25                  30                  35 gga cgc cgc tca ggg cag agc cat gag ctc ctg cgg gac ttc gag gcg      260
Gly Arg Arg Ser Gly Gln Ser His Glu Leu Leu Arg Asp Phe Glu Ala
    40                  45                  50 aca ctt ctg cag atg ttt ggg ctg cgc cgc ccg cag cct agc aag          308
Thr Leu Leu Gln Met Phe Gly Leu Arg Arg Arg Pro Gln Pro Ser Lys
55                  60                  65 agt gcc gtc att ccg gac tac atg cgg gat ctt tac cgg ctt cag tct      356
Ser Ala Val Ile Pro Asp Tyr Met Arg Asp Leu Tyr Arg Leu Gln Ser
70                  75                  80                  85 ggg gag gag gag gaa gag cag atc cac agc act ggt ctt gag tat cct      404
Gly Glu Glu Glu Glu Glu Gln Ile His Ser Thr Gly Leu Glu Tyr Pro
                90                  95                  100 gag cgc ccg gcc agc cgg gcc aac acc gtg agg agc ttc cac cac gaa      452
Glu Arg Pro Ala Ser Arg Ala Asn Thr Val Arg Ser Phe His His Glu
            105                 110                 115 gaa cat ctg gag aac atc cca ggg acc agt gaa aac tct gct ttt cgt      500
Glu His Leu Glu Asn Ile Pro Gly Thr Ser Glu Asn Ser Ala Phe Arg
        120                 125                 130 ttc ctc ttt aac ctc agc agc atc cct gag aac gag gtg atc tcc tct      548
Phe Leu Phe Asn Leu Ser Ser Ile Pro Glu Asn Glu Val Ile Ser Ser
    135                 140                 145 gca gag ctt cgg ctc ttc cgg gag cag gtg gac cag ggc cct gat tgg      596
Ala Glu Leu Arg Leu Phe Arg Glu Gln Val Asp Gln Gly Pro Asp Trp
150                 155                 160                 165
```

| | | | | | | | | | | | | | | | | |
|---|---|---|---|---|---|---|---|---|---|---|---|---|---|---|---|---|
| gaa | agg | ggc | ttc | cac | cgt | ata | aac | att | tat | gag | gtt | atg | aag | ccc | cca | 644 |
| Glu | Arg | Gly | Phe | His | Arg | Ile | Asn | Ile | Tyr | Glu | Val | Met | Lys | Pro | Pro | |
| | | | 170 | | | | | 175 | | | | | 180 | | | |
| gca | gaa | gtg | gtg | cct | ggg | cac | ctc | atc | aca | cga | cta | ctg | gac | acg | aga | 692 |
| Ala | Glu | Val | Val | Pro | Gly | His | Leu | Ile | Thr | Arg | Leu | Leu | Asp | Thr | Arg | |
| | | | | 185 | | | | | 190 | | | | | 195 | | |
| ctg | gtc | cac | cac | aat | gtg | aca | cgg | tgg | gaa | act | ttt | gat | gtg | agc | cct | 740 |
| Leu | Val | His | His | Asn | Val | Thr | Arg | Trp | Glu | Thr | Phe | Asp | Val | Ser | Pro | |
| | | | 200 | | | | | 205 | | | | | 210 | | | |
| gcg | gtc | ctt | cgc | tgg | acc | cgg | gag | aag | cag | cca | aac | tat | ggg | cta | gcc | 788 |
| Ala | Val | Leu | Arg | Trp | Thr | Arg | Glu | Lys | Gln | Pro | Asn | Tyr | Gly | Leu | Ala | |
| | | | | 215 | | | | | 220 | | | | | 225 | | |
| att | gag | gtg | act | cac | ctc | cat | cag | act | cgg | acc | cac | cag | ggc | cag | cat | 836 |
| Ile | Glu | Val | Thr | His | Leu | His | Gln | Thr | Arg | Thr | His | Gln | Gly | Gln | His | |
| 230 | | | | | 235 | | | | | 240 | | | | | 245 | |
| gtc | agg | att | agc | cga | tcg | tta | cct | caa | ggg | agt | ggg | aat | tgg | gcc | cag | 884 |
| Val | Arg | Ile | Ser | Arg | Ser | Leu | Pro | Gln | Gly | Ser | Gly | Asn | Trp | Ala | Gln | |
| | | | | 250 | | | | | 255 | | | | | 260 | | |
| ctc | cgg | ccc | ctc | ctg | gtc | acc | ttt | ggc | cat | gat | ggc | cgg | ggc | cat | gcc | 932 |
| Leu | Arg | Pro | Leu | Leu | Val | Thr | Phe | Gly | His | Asp | Gly | Arg | Gly | His | Ala | |
| | | | 265 | | | | | 270 | | | | | 275 | | | |
| ttg | acc | cga | cgc | cgg | agg | gcc | aag | cgt | agc | cct | aag | cat | cac | tca | cag | 980 |
| Leu | Thr | Arg | Arg | Arg | Arg | Ala | Lys | Arg | Ser | Pro | Lys | His | His | Ser | Gln | |
| | | 280 | | | | | 285 | | | | | 290 | | | | |
| cgg | gcc | agg | aag | aag | aat | aag | aac | tgc | cgg | cgc | cac | tcg | ctc | tat | gtg | 1028 |
| Arg | Ala | Arg | Lys | Lys | Asn | Lys | Asn | Cys | Arg | Arg | His | Ser | Leu | Tyr | Val | |
| | 295 | | | | | 300 | | | | | 305 | | | | | |
| gac | ttc | agc | gat | gtg | ggc | tgg | aat | gac | tgg | att | gtg | gcc | cca | cca | ggc | 1076 |
| Asp | Phe | Ser | Asp | Val | Gly | Trp | Asn | Asp | Trp | Ile | Val | Ala | Pro | Pro | Gly | |
| 310 | | | | | 315 | | | | | 320 | | | | | 325 | |
| tac | cag | gcc | ttc | tac | tgc | cat | ggg | gac | tgc | ccc | ttt | cca | ctg | gct | gac | 1124 |
| Tyr | Gln | Ala | Phe | Tyr | Cys | His | Gly | Asp | Cys | Pro | Phe | Pro | Leu | Ala | Asp | |
| | | | | 330 | | | | | 335 | | | | | 340 | | |
| cac | ctc | aac | tca | acc | aac | cat | gcc | att | gtg | cag | acc | ctg | gtc | aat | tct | 1172 |
| His | Leu | Asn | Ser | Thr | Asn | His | Ala | Ile | Val | Gln | Thr | Leu | Val | Asn | Ser | |
| | | | 345 | | | | | 350 | | | | | 355 | | | |
| gtc | aat | tcc | agt | atc | ccc | aaa | gcc | tgt | tgt | gtg | ccc | act | gaa | ctg | agt | 1220 |
| Val | Asn | Ser | Ser | Ile | Pro | Lys | Ala | Cys | Cys | Val | Pro | Thr | Glu | Leu | Ser | |
| | | | 360 | | | | | 365 | | | | | 370 | | | |
| gcc | atc | tcc | atg | ctg | tac | ctg | gat | gag | tat | gat | aag | gtg | gta | ctg | aaa | 1268 |
| Ala | Ile | Ser | Met | Leu | Tyr | Leu | Asp | Glu | Tyr | Asp | Lys | Val | Val | Leu | Lys | |
| | 375 | | | | | 380 | | | | | 385 | | | | | |
| aat | tat | cag | gag | atg | gta | gta | gag | gga | tgt | ggg | tgc | cgc | tga | | | 1310 |
| Asn | Tyr | Gln | Glu | Met | Val | Val | Glu | Gly | Cys | Gly | Cys | Arg | | | | |
| 390 | | | | | 395 | | | | | 400 | | | | | | | gatcaggcag tccttgagga tagacagata tacacaccac acacacacac cacatacacc    1370 acacacacac gttcccatcc actcacccac    1400

<210> SEQ ID NO 4
<211> LENGTH: 402
<212> TYPE: PRT
<213> ORGANISM: Homo sapiens

<400> SEQUENCE: 4

Met Leu Met Val Val Leu Leu Cys Gln Val Leu Leu Gly Gly Ala Ser
1               5                   10                  15

His Ala Ser Leu Ile Pro Glu Thr Gly Lys Lys Lys Val Ala Glu Ile
                20                  25                  30

Gln Gly His Ala Gly Gly Arg Arg Ser Gly Gln Ser His Glu Leu Leu

-continued

```
                35                  40                  45
Arg Asp Phe Glu Ala Thr Leu Leu Gln Met Phe Gly Leu Arg Arg Arg
 50                  55                  60
Pro Gln Pro Ser Lys Ser Ala Val Ile Pro Asp Tyr Met Arg Asp Leu
 65                  70                  75                  80
Tyr Arg Leu Gln Ser Gly Glu Glu Glu Gln Ile His Ser Thr
                 85                  90                  95
Gly Leu Glu Tyr Pro Glu Arg Pro Ala Ser Arg Ala Asn Thr Val Arg
                100                 105                 110
Ser Phe His His Glu Glu His Leu Glu Asn Ile Pro Gly Thr Ser Glu
                115                 120                 125
Asn Ser Ala Phe Arg Phe Leu Phe Asn Leu Ser Ser Ile Pro Glu Asn
130                 135                 140
Glu Val Ile Ser Ser Ala Glu Leu Arg Leu Phe Arg Glu Gln Val Asp
145                 150                 155                 160
Gln Gly Pro Asp Trp Glu Arg Gly Phe His Arg Ile Asn Ile Tyr Glu
                165                 170                 175
Val Met Lys Pro Pro Ala Glu Val Val Pro Gly His Leu Ile Thr Arg
                180                 185                 190
Leu Leu Asp Thr Arg Leu Val His His Asn Val Thr Arg Trp Glu Thr
                195                 200                 205
Phe Asp Val Ser Pro Ala Val Leu Arg Trp Thr Arg Glu Lys Gln Pro
210                 215                 220
Asn Tyr Gly Leu Ala Ile Glu Val Thr His Leu His Gln Thr Arg Thr
225                 230                 235                 240
His Gln Gly Gln His Val Arg Ile Ser Arg Ser Leu Pro Gln Gly Ser
                245                 250                 255
Gly Asn Trp Ala Gln Leu Arg Pro Leu Leu Val Thr Phe Gly His Asp
                260                 265                 270
Gly Arg Gly His Ala Leu Thr Arg Arg Arg Ala Lys Arg Ser Pro
                275                 280                 285
Lys His His Ser Gln Arg Ala Arg Lys Lys Asn Lys Asn Cys Arg Arg
290                 295                 300
His Ser Leu Tyr Val Asp Phe Ser Asp Val Gly Trp Asn Asp Trp Ile
305                 310                 315                 320
Val Ala Pro Pro Gly Tyr Gln Ala Phe Tyr Cys His Gly Asp Cys Pro
                325                 330                 335
Phe Pro Leu Ala Asp His Leu Asn Ser Thr Asn His Ala Ile Val Gln
                340                 345                 350
Thr Leu Val Asn Ser Val Asn Ser Ser Ile Pro Lys Ala Cys Cys Val
                355                 360                 365
Pro Thr Glu Leu Ser Ala Ile Ser Met Leu Tyr Leu Asp Glu Tyr Asp
370                 375                 380
Lys Val Val Leu Lys Asn Tyr Gln Glu Met Val Val Glu Gly Cys Gly
385                 390                 395                 400
Cys Arg

<210> SEQ ID NO 5
<211> LENGTH: 2943
<212> TYPE: DNA
<213> ORGANISM: Homo sapiens
<220> FEATURE:
<221> NAME/KEY: CDS
<222> LOCATION: (180)..(1721)

<400> SEQUENCE: 5
```

| | |
|---|---|
| gcaactgggg gcgccccgga cgaccatgag agataaggac tgagggccag gaagggaag | 60 |
| cgagcccgcc gagaggtggc ggggactgct cacgccaagg gccacagcgg ccgcgctccg | 120 |
| gcctcgctcc gccgctccac gcctcgcggg atccgcgggg gcagcccggc cgggcgggg | 179 |

| | | |
|---|---|---|
| atg ccg ggg ctg ggg cgg agg gcg cag tgg ctg tgc tgg tgg tgg ggg<br>Met Pro Gly Leu Gly Arg Arg Ala Gln Trp Leu Cys Trp Trp Trp Gly<br>1                          5                            10                           15 | 227 |
| ctg ctg tgc agc tgc tgc ggg ccc ccg ctg cgg ccg ccc ttg ccc<br>Leu Leu Cys Ser Cys Cys Gly Pro Pro Leu Arg Pro Pro Leu Pro<br>                   20                          25                          30 | 275 |
| gct gcc gcg gcc gcc gcc gcc ggg ggg cag ctg ctg ggg gac ggc ggg<br>Ala Ala Ala Ala Ala Ala Ala Gly Gly Gln Leu Leu Gly Asp Gly Gly<br>               35                            40                          45 | 323 |
| agc ccc ggc cgc acg gag cag ccg ccg ccg tcg ccg cag tcc tcc tcg<br>Ser Pro Gly Arg Thr Glu Gln Pro Pro Pro Ser Pro Gln Ser Ser Ser<br>    50                            55                          60 | 371 |
| ggc ttc ctg tac cgg cgg ctc aag acg cag gag aag cgg gag atg cag<br>Gly Phe Leu Tyr Arg Arg Leu Lys Thr Gln Glu Lys Arg Glu Met Gln<br>65                          70                          75                          80 | 419 |
| aag gag atc ttg tcg gtg ctg ggg ctc ccg cac cgg ccc cgg ccc ctg<br>Lys Glu Ile Leu Ser Val Leu Gly Leu Pro His Arg Pro Arg Pro Leu<br>                   85                          90                          95 | 467 |
| cac ggc ctc caa cag ccg cag ccc ccg gcg ctc cgg cag cag gag gag<br>His Gly Leu Gln Gln Pro Gln Pro Pro Ala Leu Arg Gln Gln Glu Glu<br>               100                        105                        110 | 515 |
| cag cag cag cag cag cag ctg cct cgc gga gag ccc cct ccc ggg cga<br>Gln Gln Gln Gln Gln Gln Leu Pro Arg Gly Glu Pro Pro Pro Gly Arg<br>           115                        120                        125 | 563 |
| ctg aag tcc gcg ccc ctc ttc atg ctg gat ctg tac aac gcc ctg tcc<br>Leu Lys Ser Ala Pro Leu Phe Met Leu Asp Leu Tyr Asn Ala Leu Ser<br>    130                          135                        140 | 611 |
| gcc gac aac gac gag gac ggg gcg tcg gag ggg gag agg cag cag tcc<br>Ala Asp Asn Asp Glu Asp Gly Ala Ser Glu Gly Glu Arg Gln Gln Ser<br>145                          150                        155                      160 | 659 |
| tgg ccc cac gaa gca gcc agc tcg tcc cag cgt cgg cag ccg ccc ccg<br>Trp Pro His Glu Ala Ala Ser Ser Ser Gln Arg Arg Gln Pro Pro Pro<br>               165                        170                        175 | 707 |
| ggc gcc gcg cac ccg ctc aac cgc aag agc ctt ctg gcc ccc gga tct<br>Gly Ala Ala His Pro Leu Asn Arg Lys Ser Leu Leu Ala Pro Gly Ser<br>           180                        185                        190 | 755 |
| ggc agc ggc ggc gcg tcc cca ctg acc agc gcg cag gac agc gcc ttc<br>Gly Ser Gly Gly Ala Ser Pro Leu Thr Ser Ala Gln Asp Ser Ala Phe<br>    195                          200                        205 | 803 |
| ctc aac gac gcg gac atg gtc atg agc ttt gtg aac ctg gtg gag tac<br>Leu Asn Asp Ala Asp Met Val Met Ser Phe Val Asn Leu Val Glu Tyr<br>210                          215                        220 | 851 |
| gac aag gag ttc tcc cct cgt cag cga cac cac aaa gag ttc aag ttc<br>Asp Lys Glu Phe Ser Pro Arg Gln Arg His His Lys Glu Phe Lys Phe<br>225                          230                        235                      240 | 899 |
| aac tta tcc cag att cct gag ggt gag gtg gtg acg gct gca gaa ttc<br>Asn Leu Ser Gln Ile Pro Glu Gly Glu Val Val Thr Ala Ala Glu Phe<br>                   245                          250                        255 | 947 |
| cgc atc tac aag gac tgt gtt atg ggg agt ttt aaa aac caa act ttt<br>Arg Ile Tyr Lys Asp Cys Val Met Gly Ser Phe Lys Asn Gln Thr Phe<br>           260                        265                        270 | 995 |
| ctt atc agc att tat caa gtc tta cag gag cat cag cac aga gac tct<br>Leu Ile Ser Ile Tyr Gln Val Leu Gln Glu His Gln His Arg Asp Ser<br>    275                          280                        285 | 1043 |
| gac ctg ttt ttg ttg gac acc cgt gta gta tgg gcc tca gaa gaa ggc | 1091 |

```
                Asp Leu Phe Leu Leu Asp Thr Arg Val Val Trp Ala Ser Glu Glu Gly
                    290                 295                 300 tgg ctg gaa ttt gac atc acg gcc act agc aat ctg tgg gtt gtg act          1139
Trp Leu Glu Phe Asp Ile Thr Ala Thr Ser Asn Leu Trp Val Val Thr
305                 310                 315                 320 cca cag cat aac atg ggg ctt cag ctg agc gtg gtg aca agg gat gga          1187
Pro Gln His Asn Met Gly Leu Gln Leu Ser Val Val Thr Arg Asp Gly
                325                 330                 335 gtc cac gtc cac ccc cga gcc gca ggc ctg gtg ggc aga gac ggc cct          1235
Val His Val His Pro Arg Ala Ala Gly Leu Val Gly Arg Asp Gly Pro
            340                 345                 350 tac gat aag cag ccc ttc atg gtg gct ttc ttc aaa gtg agt gag gtc          1283
Tyr Asp Lys Gln Pro Phe Met Val Ala Phe Phe Lys Val Ser Glu Val
        355                 360                 365 cac gtg cgc acc acc agg tca gcc tcc agc cgg cgc cga caa cag agt          1331
His Val Arg Thr Thr Arg Ser Ala Ser Ser Arg Arg Arg Gln Gln Ser
    370                 375                 380 cgt aat cgc tct acc cag tcc cag gac gtg gcg cgg gtc tcc agt gct          1379
Arg Asn Arg Ser Thr Gln Ser Gln Asp Val Ala Arg Val Ser Ser Ala
385                 390                 395                 400 tca gat tac aac agc agt gaa ttg aaa aca gcc tgc agg aag cat gag          1427
Ser Asp Tyr Asn Ser Ser Glu Leu Lys Thr Ala Cys Arg Lys His Glu
                405                 410                 415 ctg tat gtg agt ttc caa gac ctg gga tgg cag gac tgg atc att gca          1475
Leu Tyr Val Ser Phe Gln Asp Leu Gly Trp Gln Asp Trp Ile Ile Ala
                420                 425                 430 ccc aag ggc tat gct gcc aat tac tgt gat gga gaa tgc tcc ttc cca          1523
Pro Lys Gly Tyr Ala Ala Asn Tyr Cys Asp Gly Glu Cys Ser Phe Pro
            435                 440                 445 ctc aac gca cac atg aat gca acc aac cac gcg att gtg cag acc ttg          1571
Leu Asn Ala His Met Asn Ala Thr Asn His Ala Ile Val Gln Thr Leu
        450                 455                 460 gtt cac ctt atg aac ccc gag tat gtc ccc aaa ccg tgc tgt gcg cca          1619
Val His Leu Met Asn Pro Glu Tyr Val Pro Lys Pro Cys Cys Ala Pro
465                 470                 475                 480 act aag cta aat gcc atc tcg gtt ctt tac ttt gat gac aac tcc aat          1667
Thr Lys Leu Asn Ala Ile Ser Val Leu Tyr Phe Asp Asp Asn Ser Asn
                485                 490                 495 gtc att ctg aaa aaa tac agg aat atg gtt gta aga gct tgt gga tgc          1715
Val Ile Leu Lys Lys Tyr Arg Asn Met Val Val Arg Ala Cys Gly Cys
                500                 505                 510 cac taa ctcgaaacca gatgctgggg acacacattc tgccttggat tcctagatta          1771
His catctgcctt aaaaaaacac ggaagcacag ttggaggtgg gacgatgaga ctttgaaact        1831
atctcatgcc agtgccttat tacccaggaa gattttaaag gacctcatta ataatttgct       1891
cacttggtaa atgacgtgag tagttgttgg tctgtagcaa gctgagtttg gatgtctgta       1951
gcataaggtc tggtaactgc agaaacataa ccgtgaagct cttcctaccc tcctccccca       2011
aaaacccacc aaaattagtt ttagctgtag atcaagctat ttggggtgtt tgttagtaaa       2071
tagggaaaat aatctcaaag gagttaaatg tattcttggc taaaggatca gctggttcag       2131
tactgtctat caaaggtaga ttttacagag aacagaaatc ggggaagtgg ggggaacgcc       2191
tctgttcagt tcattcccag aagtccacag gacgcacagc ccaggccaca gccaggctc        2251 cacggggcgc ccttgtctca gtcattgctg ttgtatgttc gtgctggagt tttgttggtg       2311
tgaaaataca cttatttcag ccaaaacata ccatttctac acctcaatcc tccatttgct       2371
gtactctttg ctagtaccaa aagtagactg attacactga ggtgaggcta caaggggtgt       2431
```

```
gtaaccgtgt aacacgtgaa ggcagtgctc acctcttctt taccagaacg gttctttgac    2491
cagcacatta acttctggac tgccggctct agtacctttt cagtaaagtg gttctctgcc    2551
tttttactat acagcatacc acgccacagg gttagaacca acgaagaaaa taaaatgagg    2611
gtgcccagct tataagaatg gtgttagggg gatgagcatg ctgtttatga acggaaatca    2671
tgatttccct gtagaaagtg aggctcagat taaattttag aatattttct aaatgtcttt    2731
ttcacaatca tgtgactggg aaggcaattt catactaaac tgattaaata atacatttat    2791
aatctacaac tgtttgcact tacagctttt tttgtaaata taaactataa tttattgtct    2851
attttatatc tgttttgctg tggcgttggg ggggggccg ggcttttggg ggggggggtt    2911
tgtttggggg gtgtcgtggt gtgggcgggc gg                                  2943

<210> SEQ ID NO 6
<211> LENGTH: 513
<212> TYPE: PRT
<213> ORGANISM: Homo sapiens

<400> SEQUENCE: 6

Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
            20                  25                  30

Ala Ala Ala Ala Ala Ala Gly Gly Gln Leu Leu Gly Asp Gly Gly
        35                  40                  45

Ser Pro Gly Arg Thr Glu Gln Pro Pro Ser Pro Gln Ser Ser Ser
50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
            180                 185                 190

Gly Ser Gly Gly Ala Ser Pro Leu Thr Ser Ala Gln Asp Ser Ala Phe
        195                 200                 205

Leu Asn Asp Ala Asp Met Val Met Ser Phe Val Asn Leu Val Glu Tyr
210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
            260                 265                 270

Leu Ile Ser Ile Tyr Gln Val Leu Gln Glu His Gln His Arg Asp Ser
        275                 280                 285
```

-continued

```
Asp Leu Phe Leu Leu Asp Thr Arg Val Val Trp Ala Ser Glu Glu Gly
            290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
            340                 345                 350

Tyr Asp Lys Gln Pro Phe Met Val Ala Phe Lys Val Ser Glu Val
            355                 360                 365

His Val Arg Thr Thr Arg Ser Ala Ser Ser Arg Arg Gln Gln Ser
    370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
            420                 425                 430

Pro Lys Gly Tyr Ala Ala Asn Tyr Cys Asp Gly Glu Cys Ser Phe Pro
            435                 440                 445

Leu Asn Ala His Met Asn Ala Thr Asn His Ala Ile Val Gln Thr Leu
    450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
            500                 505                 510

His
```

```
<210> SEQ ID NO 7
<211> LENGTH: 1878
<212> TYPE: DNA
<213> ORGANISM: Homo sapiens
<220> FEATURE:
<221> NAME/KEY: CDS
<222> LOCATION: (123)..(1418)

<400> SEQUENCE: 7
gggcgcagcg gggcccgtct gcagcaagtg accgacggcc gggacggccg cctgcccct         60 ctgccacctg gggcggtgcg ggcccggagc ccggagcccg ggtagcgcgt agagccggcg        120 cg atg cac gtg cgc tca ctg cga gct gcg gcg ccg cac agc ttc gtg          167
   Met His Val Arg Ser Leu Arg Ala Ala Ala Pro His Ser Phe Val
   1               5                   10                  15 gcg ctc tgg gca ccc ctg ttc ctg ctg cgc tcc gcc ctg gcc gac ttc        215
Ala Leu Trp Ala Pro Leu Phe Leu Leu Arg Ser Ala Leu Ala Asp Phe
                20                  25                  30 agc ctg gac aac gag gtg cac tcg agc ttc atc cac cgg cgc ctc cgc        263
Ser Leu Asp Asn Glu Val His Ser Ser Phe Ile His Arg Arg Leu Arg
            35                  40                  45 agc cag gag cgg cgg gag atg cag cgc gag atc ctc tcc att ttg ggc        311
Ser Gln Glu Arg Arg Glu Met Gln Arg Glu Ile Leu Ser Ile Leu Gly
        50                  55                  60 ttg ccc cac cgc ccg cgc ccg cac ctc cag ggc aag cac aac tcg gca        359
Leu Pro His Arg Pro Arg Pro His Leu Gln Gly Lys His Asn Ser Ala
    65                  70                  75 ccc atg ttc atg ctg gac ctg tac aac gcc atg gcg gtg gag gag ggc        407
```

-continued

```
    Pro Met Phe Met Leu Asp Leu Tyr Asn Ala Met Ala Val Glu Glu Gly
    80                  85                  90                  95 ggc ggg ccc ggc ggc cag ggc ttc tcc tac ccc tac aag gcc gtc ttc       455
Gly Gly Pro Gly Gly Gln Gly Phe Ser Tyr Pro Tyr Lys Ala Val Phe
                100                 105                 110 agt acc cag ggc ccc cct ctg gcc agc ctg caa gat agc cat ttc ctc       503
Ser Thr Gln Gly Pro Pro Leu Ala Ser Leu Gln Asp Ser His Phe Leu
        115                 120                 125 acc gac gcc gac atg gtc atg agc ttc gtc aac ctc gtg gaa cat gac       551
Thr Asp Ala Asp Met Val Met Ser Phe Val Asn Leu Val Glu His Asp
130                 135                 140 aag gaa ttc ttc cac cca cgc tac cac cat cga gag ttc cgg ttt gat       599
Lys Glu Phe Phe His Pro Arg Tyr His His Arg Glu Phe Arg Phe Asp
    145                 150                 155 ctt tcc aag atc cca gaa ggg gaa gct gtc acg gca gcc gaa ttc cgg       647
Leu Ser Lys Ile Pro Glu Gly Glu Ala Val Thr Ala Ala Glu Phe Arg
160                 165                 170                 175 atc tac aag gac tac atc cgg gaa cgc ttc gac aat gag acg ttc cgg       695
Ile Tyr Lys Asp Tyr Ile Arg Glu Arg Phe Asp Asn Glu Thr Phe Arg
                180                 185                 190 atc agc gtt tat cag gtg ctc cag gag cac ttg ggc agg gaa tcg gat       743
Ile Ser Val Tyr Gln Val Leu Gln Glu His Leu Gly Arg Glu Ser Asp
            195                 200                 205 ctc ttc ctg ctc gac agc cgt acc ctc tgg gcc tcg gag gag ggc tgg       791
Leu Phe Leu Leu Asp Ser Arg Thr Leu Trp Ala Ser Glu Glu Gly Trp
        210                 215                 220 ctg gtg ttt gac atc aca gcc acc agc aac cac tgg gtg gtc aat ccg       839
Leu Val Phe Asp Ile Thr Ala Thr Ser Asn His Trp Val Val Asn Pro
225                 230                 235 cgg cac aac ctg ggc ctg cag ctc tcg gtg gag acg ctg gat ggg cag       887
Arg His Asn Leu Gly Leu Gln Leu Ser Val Glu Thr Leu Asp Gly Gln
240                 245                 250                 255 agc atc aac ccc aag ttg gcg ggc ctg att ggg cgg cac ggg ccc cag       935
Ser Ile Asn Pro Lys Leu Ala Gly Leu Ile Gly Arg His Gly Pro Gln
                260                 265                 270 aac aag cag ccc ttc atg gtg gct ttc ttc aag gcc acg gag gtc cac       983
Asn Lys Gln Pro Phe Met Val Ala Phe Phe Lys Ala Thr Glu Val His
            275                 280                 285 ttc cgc agc atc cgg tcc acg ggg agc aaa cag cgc agc cag aac cgc      1031
Phe Arg Ser Ile Arg Ser Thr Gly Ser Lys Gln Arg Ser Gln Asn Arg
        290                 295                 300 tcc aag acg ccc aag aac cag gaa gcc ctg cgg atg gcc aac gtg gca      1079
Ser Lys Thr Pro Lys Asn Gln Glu Ala Leu Arg Met Ala Asn Val Ala
305                 310                 315 gag aac agc agc agc gac cag agg cag gcc tgt aag aag cac gag ctg      1127
Glu Asn Ser Ser Ser Asp Gln Arg Gln Ala Cys Lys Lys His Glu Leu
320                 325                 330                 335 tat gtc agc ttc cga gac ctg ggc tgg cag gac tgg atc atc gcg cct      1175
Tyr Val Ser Phe Arg Asp Leu Gly Trp Gln Asp Trp Ile Ile Ala Pro
                340                 345                 350 gaa ggc tac gcc gcc tac tac tgt gag ggg gag tgt gcc ttc cct ctg      1223
Glu Gly Tyr Ala Ala Tyr Tyr Cys Glu Gly Glu Cys Ala Phe Pro Leu
            355                 360                 365 aac tcc tac atg aac gcc acc aac cac gcc atc gtg cag acg ctg gtc      1271
Asn Ser Tyr Met Asn Ala Thr Asn His Ala Ile Val Gln Thr Leu Val
        370                 375                 380 cac ttc atc aac ccg gaa acg gtg ccc aag ccc tgc tgt gcg ccc acg      1319
His Phe Ile Asn Pro Glu Thr Val Pro Lys Pro Cys Cys Ala Pro Thr
385                 390                 395 cag ctc aat gcc atc tcc gtc ctc tac ttc gat gac agc tcc aac gtc      1367
```

```
Gln Leu Asn Ala Ile Ser Val Leu Tyr Phe Asp Asp Ser Ser Asn Val
400                 405                 410                 415 atc ctg aag aaa tac aga aac atg gtg gtc cgg gcc tgt ggc tgc cac    1415
Ile Leu Lys Lys Tyr Arg Asn Met Val Val Arg Ala Cys Gly Cys His
                420                 425                 430 tag ctcctccgag aattcagacc ctttggggcc aagttttct ggatcctcca          1468 ttgctcgcct tggccaggaa ccagcagacc aactgccttt tgtgagacct tcccctccct   1528
atccccaact ttaaaggtgt gagagtatta ggaaacatga gcagcatatg cttttgatc    1588 agttttcag tggcagcatc caatgaacaa gatcctacaa gctgtgcagg caaaacctag    1648
caggaaaaaa aaacaacgca taaagaaaaa tggccgggcc aggtcattgg ctgggaagtc   1708
tcagccatgc acggactcgt ttccagaggt aattatgagc gcctaccagc caggccaccc   1768
agccgtggga ggaagggggc gtggcaaggg gtgggcacat tggtgtctgt gcgaaaggaa   1828
aattgacccg gaagttcctg taataaatgt cacaataaaa cgaatgaatg              1878

<210> SEQ ID NO 8
<211> LENGTH: 431
<212> TYPE: PRT
<213> ORGANISM: Homo sapiens

<400> SEQUENCE: 8

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
```

-continued

```
                    260                 265                 270
Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
        290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430
```

US 8,470,354 B2

OSTEOGENIC IMPLANTS WITH COMBINED IMPLANT MATERIALS AND METHODS FOR SAME

REFERENCE TO RELATED APPLICATIONS

The present application is a divisional application of U.S. patent application Ser. No. 11/361,026, filed Feb. 23, 2006, now issued as U.S. Pat. No. 7,722,895, which is a continuation application of U.S. patent application Ser. No. 11/118,124, filed Apr. 29, 2005, now abandoned, which claims the benefit of U.S. Patent Application Ser. No. 60/611,527 filed Sep. 20, 2004, each of which is hereby incorporated herein by reference in its entirety.

BACKGROUND OF THE INVENTION

The present invention resides generally in the field of implants for promoting bone growth, and in one particular aspect the invention relates to implants for promoting bone growth that contain an osteogenic protein combined with a porous matrix material.

As further background, a wide variety of therapeutic regimens are undertaken to induce the growth of bone of a patient into a desired region. Examples of such therapeutic regimens exist in the field of spinal surgery, including a variety of spinal fusion procedures. Illustratively, in posterolateral fusion procedures, bone growth is induced to fuse transverse processes of adjacent vertebrae, typically in the lumbar spine. In the predominant historic and current practice, bone of the patient harvested from the iliac crest is implanted between transverse processes of the patient to facilitate the growth of a bone mass sufficient to achieve arthrodesis. However, increased costs and risks are associated with the harvest of the patient's bone, and in some patients there may be insufficient quality iliac crest bone for the procedure. Consequently, more recent efforts in academics and industry have explored the development of procedures that minimize or eliminate the need to harvest patient bone.

In certain areas of study, implants including osteogenic proteins have been used instead of or as a supplement to autogenous bone. The use of such osteogenic proteins is itself accompanied by a variety of challenges. The active protein materials are commonly complicated to obtain or produce, costly, and highly regulated. As well, challenges are presented in determining the optimal and most effective use of the osteogenic proteins to generate relevant masses of bone for fusion or other purposes.

In light of this background, there remain needs for improved and/or alternative osteogenic implant materials as well as related materials and methods for their preparation and use. The present invention is addressed to these needs.

SUMMARY OF THE INVENTION

In certain aspects, the present invention features the discovery of an osteogenic implant configuration that effectively utilizes osteogenic protein to induce bone growth through a desired volume occupied by the implant. Accordingly, in one embodiment, the present invention provides an osteogenic implant for promoting bone growth between first and second bone surfaces. The implant includes a first resorbable implant material defining an implant body configured for receipt between the first and second bone surfaces. The first resorbable implant material includes a porous collagenous matrix containing mineral particles. The osteogenic implant also includes a second resorbable implant material covering at least a portion of the outer surface of the implant body, wherein the second material is positioned to contact the first and second bone surfaces. The osteogenic implant further includes an osteogenic protein carried by the second resorbable implant material. In certain embodiments, the osteogenic implant is configured for receipt between adjacent upper and lower transverse processes in the spine of a mammal, including a human, and/or the osteogenic protein is a bone morphogenic protein (BMP) such as BMP-2, BMP-4, BMP-6, or BMP-7. As well, the mineral particles can comprise bone, a synthetic ceramic material, or combination thereof.

Another embodiment of the invention provides a medical implant for promoting bone growth, the medical implant having an outer osteogenic implant material, the outer osteogenic implant material including a wetted, porous bioresorbable sponge matrix having sorbed therein an aqueous medium including an osteogenic protein. The implant also includes an inner scaffolding implant material including a mineral component such as an osteoconductive synthetic ceramic, the inner scaffolding implant material configured to occupy a three-dimensional volume for bone ingrowth initiated by the outer osteogenic implant material.

In another embodiment, the invention provides an implant configured to promote spinal fusion between first and second transverse processes in a patient. The implant includes a first resorbable implant material defining an implant body configured for receipt between the first and second transverse processes, wherein the first resorbable implant material includes a porous collagen-containing matrix incorporating mineral particles. A collagen sponge carrier covers at least a portion of the outer surface of the implant body and is positioned to contact the first and second transverse processes. A bone morphogenic protein is carried by the collagen sponge carrier.

In another embodiment, the invention provides an implant for promoting bone growth between first and second bone surfaces. The implant includes a first implant material containing collagen and mineral and configured to occupy a volume for bone growth. The implant further includes a second implant material covering at least a portion of the first implant material, wherein the second implant material carries an osteogenic protein.

In another aspect, the invention provides an implant suitable for carrying an osteogenic protein. The implant includes a first resorbable implant material defining an implant body and configured for receipt between first and second bone surfaces. The first resorbable implant material includes a mineral component, and can be a porous resorbable matrix incorporating mineral particles. A second resorbable implant material is provided a covering at least a portion of the outer surface of the implant body and is positioned to contact the first and second bone surfaces. In certain embodiments, the implant can be configured for use in a spinal fusion procedure in a mammal such as a human, including a posterolateral spinal fusion procedure. The first resorbable implant material can for example include a porous collagen-containing matrix incorporating mineral particles, and/or the second resorbable implant material can include a collagen sponge carrier.

Still another embodiment of invention provides a medical kit for promoting bone growth between first and second bone surfaces of a patient. The medical kit includes a first resorbable implant material comprising a mineral component such as a porous resorbable matrix having particulate mineral embedded therein. The kit further includes a second resorbable implant material configured to cover at least a portion of a surface of the first resorbable implant material, and an osteogenic protein. The kit can include other components such as one or more syringes, surgical tools, and/or surgical implants.

In another embodiment, the invention provides a method for preparing a medical implant for inducing bone growth in a patient at an implant site. The method includes the steps of providing (i) a dry, porous bioresorbable sponge matrix; (ii) an osteoconductive scaffolding material comprising a mineral component; and (iii) an aqueous formulation including an osteogenic protein. The dry, porous bioresorbable sponge matrix is wetted with the aqueous formulation so as to form a wetted bioresorbable sponge matrix having the aqueous formulation sorbed therein, and at least a portion of the osteoconductive scaffolding material is covered with the wetted bioresorbable sponge matrix.

The invention provides in another embodiment a method for inducing spinal fusion between first and second bone surfaces in a patient. The method includes providing (i) a dry, porous bioresorbable sponge matrix; (ii) an osteoconductive scaffolding material comprising a mineral component; and (iii) an aqueous formulation including an osteogenic protein. The dry, porous bioresorbable sponge matrix is wetted with an aqueous formulation so as to form a wetted bioresorbable sponge matrix having the aqueous formulation sorbed therein. The wetted bioresorbable sponge matrix is manipulated to cover at least a portion of the osteoconductive scaffolding material and form a combined implant construct. The combined implant construct includes first and second portions of the wetted porous sponge matrix positioned to contact the first and second bone surfaces, respectively, the combined implant construct further having the osteoconductive scaffolding material positioned between the first and second portions of the wetted bioresorbable sponge matrix. The method further includes implanting the combined implant construct between the first and second bone surfaces in the patient with the first and second portions of the wetted porous sponge matrix contacting the first and second bone surfaces and the osteoconductive scaffolding material occupying a volume for bone growth to create a fusion mass between the first and second bone surfaces.

In still further embodiments, the present invention provides further methods of preparing and using implants of the invention as described hereinbelow.

Additional embodiments as well as features and advantages of the invention will be apparent from the descriptions herein.

DETAILED DESCRIPTION

Figure 1:
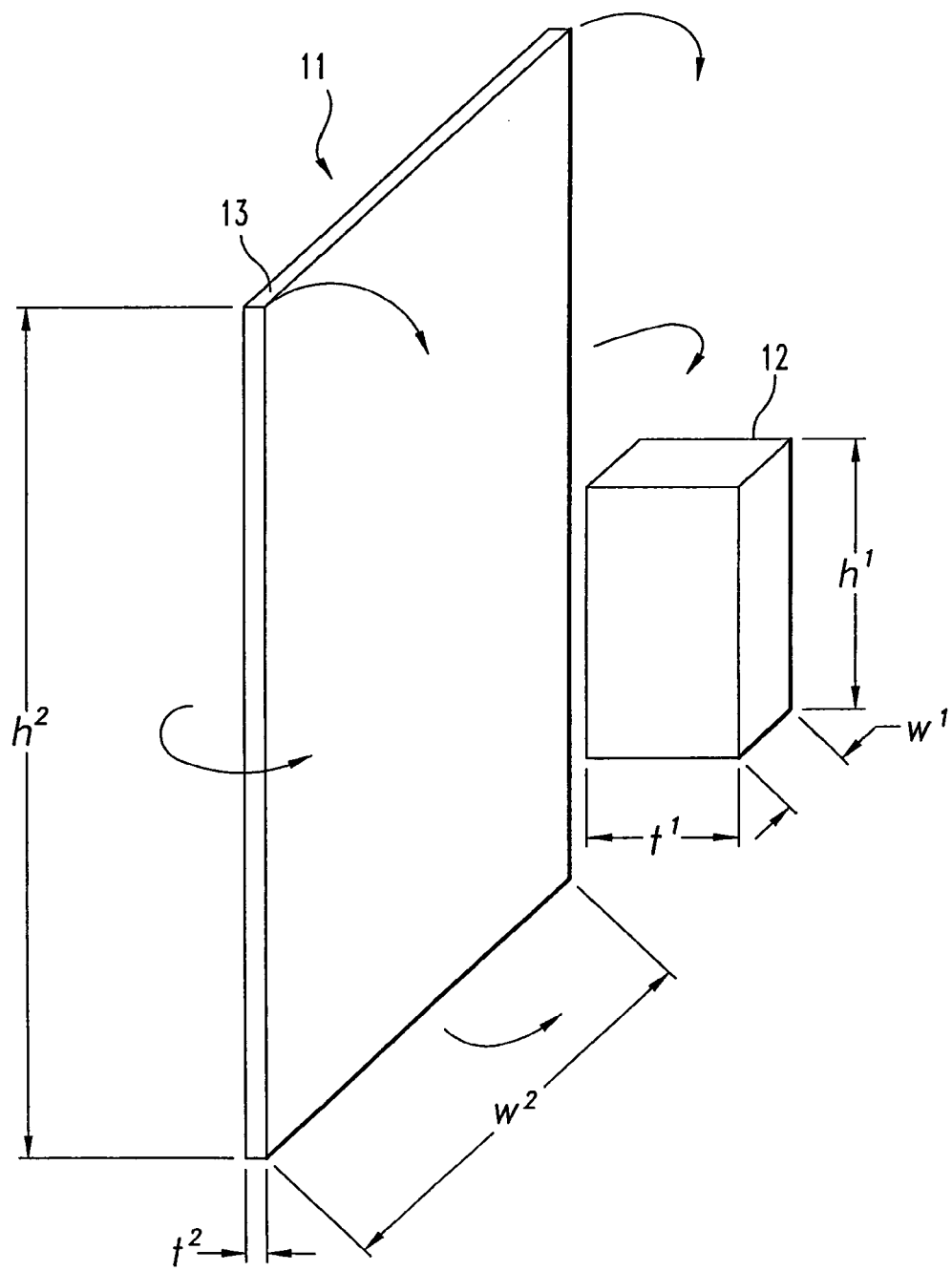
FIG. 1 provides a perspective view of first and second resorbable implant materials used to prepare an implant of the invention.

For the purposes of promoting an understanding of the principles of the invention, reference will now be made to certain embodiments thereof and specific language will be used to describe the same. It will nevertheless be understood that no limitation of the scope of the invention is thereby intended, and alterations and modifications in the illustrated implants, and further applications of the principles of the invention as illustrated herein are contemplated as would normally occur to one skilled in the art to which the invention relates.

As disclosed above, one aspect of the present invention provides osteogenic implants that include a first implant material having a surface covered at least in part by a second implant material, wherein the second implant material incorporates an osteogenic protein such as a bone morphogenic protein (BMP). In other aspects, the invention provides materials and methods for preparing and using osteogenic implants.

Implants of the invention include a first implant material including a natural and/or synthetic mineral component. For example, the mineral component can be provided by a particulate mineral material, including either powder form or larger particulate mineral materials such as granules. In certain embodiments, the particulate mineral component is effective in providing a scaffold for bone ingrowth as the resorbable matrix material is resorbed. The mineral material may for example be bone, especially cortical bone, or a synthetic bioceramic such as a calcium-containing ceramic, for example a biocompatible calcium phosphate ceramic. Illustrative ceramics thus include tricalcium phosphate, hydroxyapatite, and biphasic calcium phosphate. These mineral components may be purchased commercially or obtained or synthesized by methods known in the art. Mineral components of inventive implants can also serve as a source of calcium and/or phosphate ions for bone generation and can be incorporated at levels to regulate the compressibility of the implants.

As noted above, biphasic calcium phosphate can be used to provide the mineral component in the invention. Desirably, such biphasic calcium phosphate will have a tricalcium phosphate:hydroxyapatite weight ratio of about 50:50 to about 95:5, more preferably about 70:30 to about 95:5, even more preferably about 80:20 to about 90:10, and most preferably about 85:15.

The first implant material can include an amount of mineral that will provide a scaffold effective to remain in the patient for a period of time sufficient for the formation of osteoid in the void for which bone growth is desired. Typically, this period of time will be about 8 to about 12 weeks, although longer or shorter periods may also occur in particular situations. The minimum level of mineral that must be present in the composition is also dependent on the activity of the BMP or other osteogenic protein in the composition. Generally, the higher the activity of the protein, the greater the content of the mineral matrix required.

In certain embodiments of the invention, the first implant material includes a plurality of discrete mineral particle such as granules or may be provided by a monolithic synthetic ceramic or other mineral body dimensioned to occupy the desired three dimensional space for bone ingrowth. In other embodiments of the invention, the first implant material includes a porous matrix material incorporating mineral particles. The porous matrix material can be collagenous. A wide variety of collagen materials are suitable for these purposes. Naturally occurring collagens may be subclassified into several different types depending on their amino acid sequence, carbohydrate content and presence or absence of disulfide cross-links. Types I and III collagen are two of the most common subtypes of collagen. Type I collagen is present in skin, tendon and bone whereas Type III collagen is found primarily in skin. The collagen in the matrix may be obtained from skin, bone, tendon, or cartilage and purified by methods known in the art. Alternatively, the collagen may be purchased commercially. The porous matrix composition desirably includes Type I bovine collagen.

The collagen of the porous resorbable matrix can further be a telopeptide collagen and/or telopeptide collagen. Moreover, both non-fibrillar and fibrillar collagen may be used. Non-fibrillar collagen is collagen that has been solubilized and has not been reconstituted into its native fibrillar form.

The resorbable matrix of the first implant material may also be formed of other natural or synthetic polymeric materials, in addition to or as an alternative to collagen. For example, the resorbable matrix may comprise gelatin (e.g. foamed gelatin), or resorbable synthetic polymers such as polylactic acid polymers, polyglycolic acid polymers, or co-polymers thereof. Other natural and synthetic polymers are also known for the formation of biocompatible resorbable matrix materials, and can be used in the invention.

In certain forms of the invention, the first implant material will have a particulate mineral:resorbable porous matrix weight ratio of at least about 4:1, more typically at least about 10:1. In highly mineralized implants, the particulate mineral will constitute at least 95% by weight of the first implant material. For example, highly effective first implant materials are provided wherein they comprise about 97% to about 99% by weight particulate mineral and about 1% to about 3% of the collagen or other matrix forming material. Moreover, the mineral component in certain embodiments has an average particle size of at least about 0.5 mm, more preferably about 0.5 mm to about 5 mm, and most preferably about 1 mm to about 3 mm.

To make one form of the first implant material, a collagen slurry may be prepared as known, and can be chilled to increase its viscosity to help suspend the particulate mineral component. The particulate mineral is dispersed into the collagen slurry and gently mixed. After the particulate mineral component is uniformly dispersed in the slurry, the slurry is poured into sterile trays or other forms and freeze dried. The sheets of implant material are then removed from the freeze drier and if desired exposed to a glutaraldehyde or other cross-linking agent. The composite material formed is desirably three-dimensionally stable but flexible, and can be sterilized and packaged in accordance with known procedures.

As noted above, osteogenic implants of the invention include a second resorbable implant material covering at least a portion of the surface of the first resorbable implant material. The second implant material can include a porous matrix prepared with a matrix-forming material such as those discussed above for the first implant material. Accordingly, the second implant material may include a resorbable collagenous matrix in certain embodiments, which may incorporate any of the collagen types discussed above or any combination thereof. In a particular embodiment, the second implant material may be provided by an absorbable collagen sponge (ACS) material made with Type 1 bovine collagen and manufactured by Integra Lifesciences. As well, the resorbable matrix in the second implant material may also be formed of other natural or synthetic polymeric materials in addition to or as an alternative to collagen. Such materials may for example include gelatin or other natural or synthetic polymers (e.g. polylactic acid, polyglycolic acid, or copolymers thereof) useful for the formation of biocompatible resorbable matrix materials. The second resorbable implant material may also include a mineral component, which may be the same as or different from that of the first resorbable implant material.

As indicated above, osteogenic implants of the invention include an osteogenic protein carried in the second implant material; for example, the osteogenic protein can be a bone morphogenic protein (BMP). Recombinant human BMPs can be used, and may be commercially obtained or prepared as described and known in the art, e.g. in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al. The osteogenic protein may be isolated from tissue sources such as bone. Methods for isolating BMP from bone are described, for example, in U.S. Pat. No. 4,294,753 to Urist and Urist et al., PNAS 371, 1984.

In some embodiments, the osteogenic protein will include a pair of polypeptides having amino acid sequences each comprising a sequence that shares a defined relationship with an amino acid sequence of a reference morphogenic protein. Desirable osteogenic polypeptides for use in the present invention have an amino acid sequence that shares a defined relationship with a sequence present in osteogenically active human BMP-2 (SEQ ID NO: 2; see also National Center for Biotechnological Information (NCBI) Accession No. P12643), osteogenically active human BMP-4 (SEQ ID NO: 4; see also NCBI Accession Nos. P12644, and BAA06410), osteogenically active human BMP-6 (SEQ ID NO: 6; see also NCBI Accession No. P22004), or osteogenically active human BMP-7 (SEQ ID NO: 8; see also NCBI Accession No. P18075). However, any one or more of the naturally occurring or biosynthetic sequences disclosed herein similarly could be used as a reference sequence. Polypeptides in a dimeric protein with osteogenic activity can each comprise a sequence that corresponds to a reference sequence or that is functionally equivalent thereto.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. Functionally equivalent sequences further include those wherein one or more amino acid residues differs from the corresponding residue of a reference sequence, e.g., the C-terminal cysteine domain (also referred to herein as the conserved cysteine skeleton) of human BMP-2, provided that this difference does not destroy bone morphogenic activity. Conservative substitutions of corresponding amino acids in the reference sequence may be used. Amino acid residues that are conservative substitutions for corresponding residues in a reference sequence are those that are physically or functionally similar to the corresponding reference residues, e.g., that have similar size, shape, electric charge, chemical properties including the ability to form covalent or hydrogen bonds, or the like. Common conservative substitutions are those fulfilling the criteria defined for an accepted point mutation in Dayhoff et al. (1978), 5 Atlas of Protein Sequence and Structure, Suppl. 3, ch. 22 (pp. 354-352), Natl. Biomed. Res. Found., Washington, D.C. 20007.

Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. The term "conservative variation" also includes the use of a substituted amino acid in place of an unsubstituted parent amino acid provided that antibodies raised to the substituted polypeptide also immunoreact with the unsubstituted polypeptide.

As described above, particularly useful sequences for the present invention include those comprising the sequences for BMP-2 or BMP-4 (see WO88/00205, U.S. Pat. No. 5,013,649 and WO91/18098), BMP6 (see WO90/11366, PCT/US90/01630), and BMP-7 (also referred to as OP1, see U.S. Pat. No. 5,011,691 and Oppermann et al.), and functionally equivalent sequences thereto.

Publications disclosing these sequences, as well as their chemical and physical properties, include: BMP-2 and BMP-4: WO88/00205, Wozney et al. (1988) Science 242:1528-1534); BMP-7 (OP-1): U.S. Pat. No. 5,011,691, U.S. Pat. No. 5,266,683, Ozkaynak et al. (1990) EMBO J. 9: 2085-2093; and BMP-6: Celeste et al. (1991) PNAS 87: 9843-9847. Recombinant human BMP-2 (rhBMP-2), recombinant human BMP-4 (rhBMP-4), recombinant human BMP-6, recombinant human BMP-7 (rhBMP-7) or heterodimers thereof, may be used to particular advantage. It will be understood, however, that other BMP proteins may be used in the present invention, including for example BMP-9.

In other embodiments, useful proteins include biologically active biosynthetic constructs, including novel biosynthetic morphogenic proteins and chimeric proteins designed using sequences from two or more known morphogens.

In certain embodiments, bone morphogenic proteins useful in aspects of the invention include those in which the amino acid sequences comprise a sequence sharing at least 70% amino acid sequence homology or "similarity", and preferably 80% homology or similarity, with a reference morphogenic protein selected from the foregoing naturally occurring proteins. Preferably, the reference protein is human BMP-2, human BMP-4, human BMP-6, or human BMP-7, and the reference sequence thereof is the C-terminal cysteine domain present in osteogenically active forms of these proteins. A polypeptide suspected of being functionally equivalent to a reference morphogen polypeptide can be aligned therewith using the method of Needleman, et al. (1970) J. Mol. Biol. 48:443-453, implemented conveniently by computer programs such as the Align program (DNAstar, Inc.). Internal gaps and amino acid insertions in the candidate sequence are ignored for purposes of calculating the defined relationship, conventionally expressed as a level of amino acid sequence homology or identity, between the candidate and reference sequences. "Amino acid sequence homology" is understood herein to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. In a currently preferred embodiment, the reference sequence is BMP-2. Bone morphogenic proteins useful herein accordingly include allelic, phylogenetic counterpart and other variants of the preferred reference sequence, whether naturally-occurring or biosynthetically produced (e.g., including "muteins" or "mutant proteins"), as well as novel members of the general morphogenic family of proteins, including those set forth and identified above. Certain particularly preferred morphogenic polypeptides share at least 60% amino acid identity with the preferred reference sequence of human BMP-2, still more preferably at least 80% amino acid identity therewith.

In still other embodiments, useful osteogenically active proteins have polypeptide chains with amino acid sequences comprising a sequence encoded by a nucleic acid that hybridizes, under any or all of low, medium or high stringency hybridization conditions, to DNA or RNA encoding reference morphogen sequences, e.g., C-terminal sequences defining the conserved seven cysteine domains of BMP-2 (SEQ. ID NO. 1; see also NCBI Accession No. NM001200), BMP-4 (SEQ. ID NO. 3; see also NCBI Accession Nos. NM001202; NM130850; and NM130851), BMP-6 (SEQ. ID NO. 5; see also NCBI Accession No. NM001718) or BMP-7 (SEQ. ID NO. 7; see also NCBI Accession No. NM001719), and the like. As used herein, high stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringency conditions are well characterized in commercially available, standard molecular cloning texts. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984): Nucleic Acid Hybridization (B. D. Hames & S. J. Higgins eds. 1984); and B. Perbal, A Practical Guide To Molecular Cloning (1984).

Proteins useful in the present invention generally are dimeric proteins comprising a folded pair of polypeptides. Such morphogenic proteins are inactive when reduced, but are active as oxidized homodimers and when oxidized in combination with others of this invention to produce heterodimers. Thus, members of a folded pair of morphogenic polypeptides in a morphogenically active protein can be selected independently from any of the specific polypeptides mentioned above.

Bone morphogenic proteins useful in the invention include proteins comprising any of the polypeptide chains described above, whether isolated from naturally-occurring sources, or produced by recombinant DNA or other synthetic techniques, and includes allelic and phylogenetic counterpart variants of these proteins, as well as muteins thereof, and various truncated and fusion constructs. Deletion or addition mutants also are envisioned to be active, including those that may alter the conserved C-terminal cysteine domain, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The bone morphogenic proteins contemplated herein can be expressed from intact or truncated cDNA or from synthetic DNAs in prokaryotic or eukaryotic host cells, and purified, cleaved, refolded, and dimerized to form morphogenically active compositions. Candidate host cells include, without limitation, prokaryotes including E. coli, or eukaryotes including yeast, or mammalian cells, such as CHO, COS or BSC cells. One of ordinary skill in the art will appreciate that other host cells can be used to advantage. Detailed descriptions of specific bone morphogenic proteins useful in the practice of this invention, including how to make, use and test them for osteogenic activity, are disclosed in numerous publications, including for example those referenced hereinabove. Additional osteogenic proteins that may be used in aspects of the present invention are included in the group of osteogenic proteins identified in U.S. patent application Ser. No. 09/045,331 filed Mar. 20, 1998, published Aug. 23, 2001 as US 20010016646 A1.

Other therapeutic growth factors may also be used in accordance with the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-α and TGF-β.

Thus, in view of this disclosure and the knowledge available in the art, skilled genetic engineers can isolate genes from cDNA or genomic libraries of various different biological species, which encode appropriate amino acid sequences, or construct DNAs from oligonucleotides, and then can express them in various types of host cells, including both prokaryotes and eukaryotes, to produce large quantities of active proteins capable of stimulating endochondral bone morphogenesis in a mammal.

In one mode of preparing osteogenic implants of the invention, the second implant material can be positioned over a surface of a body of the first implant material, either before or after the osteogenic protein has been incorporated into the second implant material. For example, a sheet of the second implant material having the osteogenic protein incorporated therein can be wrapped around a block or other substantial three dimensional volume of the first implant material, to prepare an osteogenic implant of the invention. In certain modes of practicing the invention, the osteogenic implant including the combination of the first and second resorbable implant materials can be sized for receipt at a location between two adjacent vertebrae of a mammal, including a human, and can be configured to facilitate fusion of the two vertebrae. In one specific embodiment, the osteogenic implant is configured for insertion between adjacent transverse processes of a human patient, e.g. in the lumbar spine, so as to occupy the spatial volume therebetween with the second material incorporating the osteogenic protein in contact with the transverse processes. Implants so configured can be effectively used to achieve posterolateral fusion in human or other patients in need thereof, including lumbar posterolateral fusion. Such posterolateral fusion procedures can be performed as open surgical procedures or minimally invasive procedures, and can be instrumented or non-instrumented. Minimally invasive procedures can be facilitated by specialized systems, such as the CD Horizon® Sextant percutaneous rod insertion system available from Medtronic Sofamor Danek.

Implants of the invention can also be used in other spinal fusion procedures including anterior and posterior lumbar spinal fusion procedures. For example, implants of the invention can be used on the lamina in posterior fusion or within the disc space, e.g. in interbody fusion techniques. Relatedly, implants of the invention can be used in conjunction with load bearing spinal implants such as fusion cages, and may serve to induce bone growth in, through and/or around such load bearing spinal implants.

Still further, implants of the invention can be used to promote bone growth from and between bone surfaces in other areas of the body, including for example in the repair of long bone defects or cranial defects, including but not limited to the repair of simple and compound fractures and non-unions.

Figure 2:
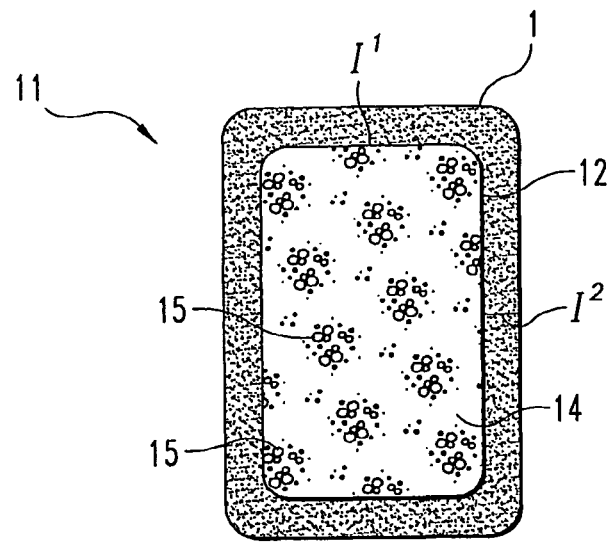
FIG. 2 provides a cross-sectional view of an implant of the invention including first and second resorbable implant materials.
Figure 3:
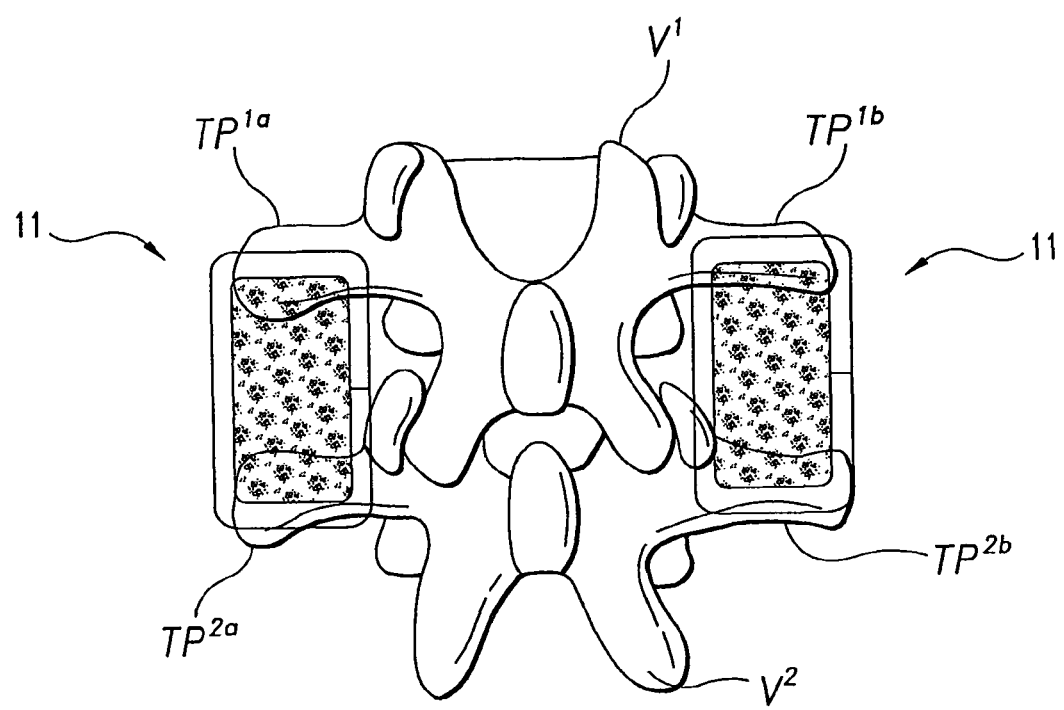
FIG. 3 provides a view of an implant of the invention configured for posterolateral fusion received between first and second transverse processes of a human patient.

With reference now to FIGS. 1-3, an illustrative osteogenic implant 11 of the invention will be described. Osteogenic implant 11 includes a first implant material 12 forming an implant body for occupying a substantial three-dimensional volume through which bone growth is desired. First implant material 12 can, for example, have a height $h^1$ of about 1 cm to about 10 cm, a width $w^1$ of about 0.5 cm to about 2 cm, and a thickness $t^1$ of about 0.5 cm to about 1.5 cm. Implant 11 also includes a second implant material 13 generally in sheet form, that is used to cover at least a portion of the outer surface of implant material 12 and can in certain embodiments completely encase and cover all surfaces of implant material 12. As illustrated in FIG. 1, sheet form implant material 13 can be folded around implant material 12 (see arrows) to form an osteogenic implant of the present invention including combined first and second matrix materials. Implant material 13 can have suitable dimensions for this purpose, for example having a height $h^2$ of about 1 cm to about 10 cm, a width $w^2$ of about 1 cm to about 10 cm, and a thickness $t^2$ of about 0.2 cm to about 0.5 cm. Unless stated otherwise, the dimensions given herein for the first implant material 12 and the second implant material 13 are their dimensions when wet (saturated).

With particular reference now to FIG. 2, shown is implant 11 of the invention including first implant material 12 encased by implant material 13. Implant material 12 in the illustrated embodiment includes a matrix forming material 14 and mineral particles 15 embedded therein. Second implant material 13 is shown wrapped around first implant material 12 forming an interface $I^1$ therebetween. In the illustrated embodiment, second implant material 13 wraps completely around first implant material 12 and contacts itself at interface $I^2$. In accordance with aspects of the present invention, second implant material 13 will be impregnated with a liquid carrier including an osteogenic protein such as a BMP, and first implant material 12, at least as the implant 11 is assembled, will be free or substantially free from the osteogenic protein incorporated in second implant material 13. It is expected in this regard that once implant 11 is assembled, some level of diffusion of osteogenic protein across interface $I^1$ may occur; however, in certain embodiments of the invention, it is nonetheless expected that at least a substantial internal volume of the implant body formed from first implant material 12 will remain essentially free from any such osteogenic protein and will be osteoconductive and not osteoinductive in nature. As well, in the illustrated embodiment, first implant material 12 contains mineral particles 15, whereas second implant material 13 is free of mineral particles, while the matrix forming material of implant materials 12 and 13 may be the same, e.g., collagen. In such an arrangement, the first implant material 12 can be more resistant to compressive forces than second implant material 13, with both structures maintaining three-dimensional stability and a flexible or pliable nature. Such implants are advantageously facile in use, and in effectively utilizing osteogenic proteins such as BMPs dosed to the patient with implant 11.

Referring now to FIG. 3, shown are two osteogenic implants 11 of the invention in a schematic representation wherein they can facilitate posterolateral fusion in a human patient. A bilateral fusion is shown, between a first vertebra $V^1$ and a second vertebra $V^2$. In such a procedure, a first osteogenic implant 11 traverses the space between a transverse process $TP^{1a}$ of $V^1$ and transverse process $TP^{2a}$ of $V^2$. A similar arrangement is shown on the opposite side wherein an implant 11 contacts transverse process $TP^{1b}$ of the $V^1$ and transverse process $TP^{2b}$ of vertebrae $V^2$, and traverses the space therebetween. Osteogenic implants 11 thereby induce bone growth from the surfaces of the contacted transverse processes, which bone growth effectively extends through the volume occupied by the osteogenic implants 11, resulting in arthrodesis of the transverse processes and fusion of vertebrae $V^1$ with vertebrae $V^2$. If desired, for such procedures the surfaces of the involved transverse processes may be decorticated to facilitate the fusion process. Techniques and implements for decortication are well known to those of ordinary skill in the art and can be used within the scope of the invention.

The dimensions of implant bodies formed from the first implant material may vary depending on the application. For posterolateral fusion devices for humans, these dimensions may for example be about 3 cm to about 6 cm in height ($h^1$), about 1 cm to about 2 cm in width ($w^1$), and about 0.5 to about 1.5 cm in thickness ($t^1$). The dimensions for the second implant material may likewise vary. Illustrative implant devices for posterolateral fusion for humans can include an implant body of the first implant material sized as noted above, combined with a second implant material having a height ($h^2$) of about 3 cm to about 6 cm, a width ($w^2$) of about 3 to about 7 cm, and a thickness ($t^2$) of about 0.2 cm to about 0.5 cm. The total volume of implant material (first plus second implant material) for human posterolateral fusion implants will be sufficient to provide the desired fusion mass (e.g. including one level or two level fusions), and may for example range from about 5 cubic centimeters (cc's) to about 20 cc's when the implant materials are wet (saturated).

In this same vein, the total dose of osteogenic protein included in an osteogenic implant of the invention will be sufficient to induce the desired bone growth through the volume occupied by the implant. In a posterolateral fusion implant, the total dose of osteogenic protein will be sufficient to induce the desired intertransverse process fusion mass in combination with the implant, and in the case of a bone morphogenic protein such as BMP-2 (including recombinant human BMP-2, rhBMP-2) this total dose may for example not exceed about 12 mg, e.g. typically range from about 1 mg to about 12 mg, more typically about 3 mg to about 9 mg, including in human fusions. As noted above, this dosed amount of osteogenic protein may be distributed regionally within the implant material. Thus, all or substantially all of this dosed protein may be carried by the second implant material; or, in certain other embodiments, the second implant material may carry a concentration (mg per cc of implant material) that is higher than the concentration carried by the first implant material. In any case, the osteogenic protein may be substantially homogeneously distributed through the first and/or second implant material, or may be regionally concentrated within the implant material, e.g. as a coating.

It will be understood that implants of the invention may also include more than one piece of the first or second implant material. For example, multiple pieces of the first implant material may be wrapped within a single piece of the second implant material, or multiple pieces of the second implant material may cover various portions of the surface of a monolithic implant body formed from the first implant material. Illustratively, separate pieces of the second implant material carrying the osteogenic protein may be positioned overtop a monolithic body of the first implant material and positioned to contact bone surfaces to be fused.

Figure 4:
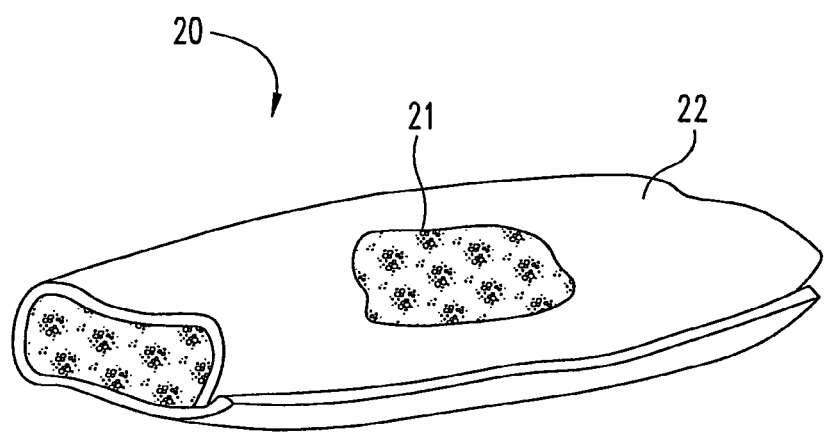
FIG. 4 provides a perspective partial cutaway view of another combined implant construct of the invention.

Another embodiment of the invention, in which the first implant material is provided as multiple pieces rather than a single piece, is shown in FIG. 4. In particular, implant construct 20 includes a first (inner) implant material constituted by a plurality of discrete ceramic granules 21, for example synthetic biphasic calcium phosphate granules 21. These granules are present in sufficient quantity to occupy a desired three-dimensional volume into which bone growth is desired, for example a volume into which a spinal fusion mass such as an interbody fusion mass or a posterolateral fusion mass. Granules 21 provide the first implant material, which is wrapped within a second (outer) implant material 22 which is preferably provided by a porous sponge matrix, especially a porous collagen sponge matrix. The second implant material carries an osteogenic protein such as a BMP. In certain embodiments, an aqueous formulation including the BMP or other osteogenic protein is used to wet the first implant material, such that the formulation is sorbed into the implant material. The implant construct 20 can thereafter be implanted into a patient so that the second implant material 22 carrying the osteogenic protein contacts bone surfaces to be fused together, whereupon the growth of a fusion bone mass is induced. In one embodiment, implant construct 20 can be configured for posterolateral spinal fusion, having a length sufficient to traverse the spinous processes to be fused.

One particularly advantageous implant that can be used for human spinal fusion, including posterolateral fusion, has a BMP such as rhBMP-2 in a liquid solution dispersed substantially homogeneously through the second implant material to provide a concentration of at least about 0.4 mg/cc based upon the wet (saturated) volume of the implant, more preferably at least about 0.6 mg/cc, e.g. in the range of about 0.6 mg/cc to about 4 mg/cc, with the first implant material being free from the osteogenic protein other than that which might diffuse from the second material into the first material upon contact between the two materials, e.g. during preparation, implantation or residence in the patient. Such implants can be prepared, for instance, by infusing the second implant material with a solution of the osteogenic protein and thereafter positioning it around the first implant material.

In certain embodiments, measures are taken to localize the majority of the osteogenic protein to the second (outer) implant material and minimize substantial diffusion therefrom that might deleteriously reduce the concentration of osteogenic protein (in mg per cc of wet implant material) in the outer regions of the overall implant that contact and initiate bone growth from adjacent bone surfaces. For example, the second implant material can be effective to bind the BMP or other osteogenic protein by ionic and/or hydrogen bonding or other bonding forces. For example, collagenous sponge material exhibits the capacity to bind BMPs such as BMP-2 in a non-covalent fashion, and the amount of protein that is effectively retained by the material against fusion or wash-out increases over the time of contact with an aqueous BMP formulation. Thus, embodiments of the invention are provided wherein an aqueous formulation of the BMP or other osteogenic protein is applied to the second implant material and allowed to equilibrate for a period of time prior to contact with the first implant material. This equilibration period can last for at least about 2 minutes, at least about 5 minutes, and is typically in the range of about 5 to about 30 minutes.

The equilibration or other protein retaining technique will desirably maintain at least about 70% by weight of the BMP or other osteogenic protein localized to the second implant material at least during the manipulation and implantation of the combined implant construct into the patient. In certain embodiments, at least about 80% by weight of the osteogenic protein will be so retained, even at least about 90% or more. It will thus be understood that certain amounts of the osteogenic protein may migrate from the second implant material in these embodiments, including for example some level of diffusion into the first implant material; however, in these embodiments any amount of osteogenic protein in the first implant material due to diffusion or otherwise will be relatively low compared to that in the second implant material, and the osteogenic protein applied to the second implant material will be substantially retained therein at least to the point of implant as discussed above. In this manner, an effective, high spatial concentration of the BMP or other osteogenic protein can be maintained at the outer regions thereof sufficient to stimulate bone ingrowth from bone surfaces that are contacted.

The present invention also includes kits for promoting bone growth in patients, wherein the kits include a first implant material as described herein, a second implant material as described herein, and an osteogenic protein as described herein. Each of such components of the kit may be provided for example in a lyophilized or otherwise dry state, or in a wet state. The kits can include a structural element in which the components are stably held spaced from one another, in a sterile, medically acceptable packaging system. Such kits can likewise include instructions for use of the kit components for promoting bone growth within a patient, for example a spinal fusion procedure such as a posterolateral spinal fusion procedure. Kits of the invention can thus also include other components such as syringes, vials, surgical instruments for minimally invasive or open techniques, spinal rods, spinal cages or other load-bearing interbody fusion devices, spinal plates, bone screws, and the like.

The invention will now be described with reference to certain specific Examples. It will be understood that these Examples are illustrative and not limiting of the invention.

EXAMPLE 1

Preparation of Collagen Sponge/Bone Particle Composite 12 grams of biphasic calcium phosphate particles (containing 85% tricalcium phosphate and 15% hydroxyapatite), 1 mm in diameter, are added to 12 grams of collagen slurry (0.192 grams of collagen). This composite slurry is poured into a 7.5 cm×10.0 cm mold, freeze dried, double sterile packaged, and sterilized by ETO gas sterilization.

EXAMPLE 2

Posterolateral Fusions Using Combined Matrix Implants 2.1 Materials and Methods

The entire protocol for this Example was reviewed and approved by the Institutional Animal Care and Use Committee for Emory University.

2.1.1 Surgical Procedure

Nine skeletally mature rhesus macaques underwent single level posterolateral intertransverse process spinal arthrodesis under general anesthesia. Anesthesia was induced with 3-5 mg/kg of intramuscular or subcutaneous telazol, and maintained with 1%-2% inhalational halothane. The monkeys were placed prone on the operating table with chest supports, then shaved, prepped and draped in a sterile manner for lumbar surgery.

A manual palpation of the iliac crests was used to estimate the L4-5 vertebral level using a preoperative lateral plain film. Subsequently, 10 mL of bupivicane was used to infiltrate the lumbodorsal region, and a midline incision was made to expose the lumbodorsal fascia. Bilateral fascial incisions were made approximately 2-3 cm off the midline, and a Wiltse muscle-splitting technique was used to develop the plane between the multifidous and logissiumus muscles. The transverse processes of L4 and L5 and the intertransverse membrane were exposed, while leaving the facet joints intact. The dorsal aspects of the L4 and L5 transverse processes were decorticated using a high-speed burr, until bleeding surfaces with cancellous bone were noted. Graft materials (see below) were then placed in the paraspinal muscle bed between the transverse processes. Absorbable 3-0 sutures were used to close the fascia, and the skin was closed using both staples and 3-0 absorbable sutures.

Animals received 0.1 mg/kg bupinorphine when indicated for postoperative pain control and were individually housed. There was no postoperative restriction on activity and no supportive orthotic devices were used. The monkeys were fed a regular diet on a routine basis for the animal facility.

Recombinant human bone morphogenic protein-2 (rh-BMP-2) (Medtronic Sofamor Danek, Memphis Term.) was delivered from a stock concentration of 1.5 or 3.0 mg/mL. The compression resistant matrix (CRM) (Medtronic Sofamor Danek, Memphis Term.) was comprised of a bovine type I collagen sponge impregnated with 15% hydroxyapatite/85% tricalcium phosphate ceramic granules, and was prepared generally as described in Example 1. The CRM block was 3.5 cm in height, and 1.2 cm in both width and thickness. The total volume of the CRM implant was about 5.0 cc. The dimensions of the dry absorbable collagen sponge (Medtronic Sofamor Danek, Memphis, Tenn.) were 5×3.8×0.35 cm.

The animals were divided into three groups (n=3 for each group) and had one of the following graft configurations implanted bilaterally as described above: 1) rhBMP-2 (10 mg per side) delivered directly on the CRM carrier; 2) rhBMP-2 (3 mg/side) delivered directly on the CRM carrier; and 3) rhBMP-2 (3 mg/side) delivered on the absorbable collagen sponge, allowed to equilibrate for about 15 minutes, and then wrapped around a block of CRM carrier.

2.1.2 Assessment of Spine Fusion

All animals were euthanized at 24 weeks postoperatively with intravenous pentobarbital. Subsequently, the lumbar spines were removed, and arthrodesis was assessed blindly by 4 methods: 1) manual palpation, 2) posteroanterior plain radiographs, 3) computerized tomography (CT), and 4) undecalcified histology.

After harvesting, the lumbar spines were manually palpated at the level of attempted fusion by a blinded observer. The observer also palpated the superior and inferior adjacent motion segments. Each motion segment was considered fused only if there was no motion present, otherwise it was graded as not fused.

Radiographs of each spine were made using a tube to plate distance of 90 cm. The radiographs were then reviewed in a blinded method; only those radiographs showing a continuous pattern of trabecular bone in the intertransverse fusion mass were graded as fused.

All lumbar spine specimens underwent CT scans in the region of the arthrodesis. A high speed spiral CT scanner (GE, Milwaukee, Wis.) was utilized, using the following parameters: 100 cm field of view, 150 mA, 100 kV, 1 mm gap, and 1 mm slice thickness. The continuity of the fusion mass and any bone formation outside the fusion mass were evaluated.

Histologic analysis was performed after the lumbosacral spines were fixed for 24 hours in a 10% neutral-buffered solution. The specimens were then placed in 70% ethanol, trimmed, and sequentially dehydrated in 95% and 100% ethanol. This step was followed by a xylene treatment. The specimens were then divided in half in the midsagittal plane, embedded in methylmethacrylate, and sectioned to 25 micrometer thickness in a sagittal or coronal plane using an automated system Exakt Technologies, Inc., Oklahoma City, Okla.). The sections were stained with 1% methylene blue and 0.3% basic fuchsin. The sections were then evaluated for the presence of newly formed trabecular bone. Histologic fusion was considered to be present if there was continuous new bridging bone across the carrier connecting the two transverse processes.

2.2 Results 2.2.1 Manual Palpation

All animals survived surgery and had uneventful postoperative courses. The three monkeys that received 10 mg of rhBMP-2 on the CRM carrier achieved solid fusions. The three monkeys that had 3 mg rhBMP-2 implanted on the CRM carrier did not achieve solid fusions. The three monkeys that received 3 mg rhBMP-2 on the absorbable collagen sponge which was then wrapped around the CRM carrier achieved solid fusions.

2.2.2 Radiographs

Serial plain radiographs were taken at 4-6 week intervals and confirmed the manual palpation results. Early fusion masses were visible on the plain films by 12 weeks and by 8 weeks on CT scans in most cases. The serial CT scan results also paralleled the plain radiographs. It was much easier to interpret the presence and extent of new bone formation in the posterolateral spine using CT scans. The three monkeys that did not achieve solid fusions with the 3 mg rhBMP-2 placed directly on the CRM carrier showed some spotty bone formation, especially around the decorticated transverse processes, but it was minimal and not nearly enough to form a continuous bridge of bone.

2.2.3 Histology

Histologic analysis of the fusion masses demonstrated consistent findings with the CT scans. Normal appearing mature trabecular bone was present with marrow cavities in the six monkeys with solid spine fusions. There was no evidence of abnormal inflammatory cells or other reaction to the carrier. In the six animals with the solid fusions, the CRM carrier had been completely remodeled. In the three animals with the nonunions, most of the CRM carrier had been resorbed.

EXAMPLE 3

Medical Kit and Preparation of Combined Implant Material Constructs

A medical kit is provided including a vial containing sterile lyophilized rhBMP-2 (12 mg); a collagen sponge (Absorbable Collagen Sponge (ACS), Integra Lifesciences) 3"×4" in size (7.5 cm×10 cm) packaged in a tray; a vial containing sterile water for injection (10 ml); two 10 ml syringes; two 20 G 1½" needles; and instructions as to the following preparation.

Using one of the needles and a 10 ml syringe, the rhBMP-2 is reconstituted with 8.4 ml of sterile water for injection in a vial. The rhBMP-2 is gently swirled in the vial during reconstitution. The ACS is cut in half making two pieces each dimensioned 2"×3". The ACS is placed in the packaging tray. Using a second needle and 10 ml syringe, 4 ml of rhBMP-2 are withdrawn from the vial. 4 ml of rhBMP-2 solution is distributed onto one 2"×3" piece of ACS. The second needle/syringe is used to withdraw another 4 ml of the rhBMP-2 solution from the vial, which is distributed uniformly onto the second piece of ACS. The ACS pieces are allowed to stand for a minimum of 15 minutes (and should be used for implantation within the next 60 minutes). A 10 cc vial of MasterGraf™ granules (10 cc, biphasic calcium phosphate having an 85:15 tricalcium phosphate:hydroxyapatite ratio) is divided into two equal 5 cc portions. The 5 cc granule portions are each distributed onto one of the 2"×3" wetted ACS pieces. Using forceps, the rhBMP-2 soaked ACS with MasterGraft™ granules are each rolled into a 2" wide roll with the ACS surrounding the MasterGraft granules. The combined implant constructs so prepared can be used in a spinal interbody fusion procedure, potentially in combination with metal cages into which the constructs are inserted, or in a posterolateral spinal fusion procedure.

While the invention has been illustrated and described in detail in the foregoing description, the same is to be considered as illustrative and not restrictive in character, it being understood that only certain embodiments have been shown and described and that all changes and modifications that come within the spirit of the invention are desired to be protected. In addition, all publications cited herein are hereby incorporated by reference in their entirety as if each had been individually incorporated by reference and fully set forth.

What is claimed is:

1. A medical implant device, comprising:
an implant structure including a first resorbable implant component combined with a second resorbable implant component, the first resorbable implant component comprising a scaffold material comprising ceramic particles, which comprise tricalcium phosphate and hydroxyapatite in a weight ratio of tricalcium phosphate to hydroxyapatite of about 50:50 to about 95:5, the first resorbable implant component comprising a particulate mineral to resorbable porous matrix weight ratio of at least about 10:1, where the ceramic particles resorb more slowly than the second resorbable implant component when the implant structure is implanted in a patient thereby remaining at the implant site for a sufficient period for tissue ingrowth, wherein the second resorbable implant component comprises a polymer sponge carrier, an osteogenic protein and substantially no ceramic particles.

2. The medical implant device of claim 1, wherein the first resorbable implant component comprises a polymer.

3. The medical implant device of claim 1 wherein the first component provides a scaffold that remains in the patient for longer than 12 weeks.

4. The medical implant device of claim 1, wherein the second resorbable implant component is wrapped around the first resorbable implant component.

5. The medical implant device of claim 1, wherein the weight ratio of tricalcium phosphate to hydroxyapatite is about 95:5.

6. A medical implant device, comprising:
an implant structure including first resorbable implant component combined with a second resorbable implant component, the first resorbable implant component comprising a scaffold material comprising mineral particles, which comprise tricalcium phosphate and hydroxyapatite in a weight ratio of tricalcium phosphate to hydroxyapatite of about 50:50 to about 95:5, the first resorbable implant component comprising a particulate mineral to resorbable porous matrix weight ratio of at least about 10:1, where the ceramic particles resorb more slowly than the second implant component when the implant structure is implanted in a patient thereby remaining at the implant site for a sufficient period for tissue ingrowth and the second resorbable implant component comprises a polymer sponge carrier, an osteogenic protein, and substantially no mineral particles.

7. The medical implant device of claim 6, wherein the first resorbable implant component comprises a polymer.

8. The medical implant device of claim 6 wherein the first component provides a scaffold that remains in the patient for longer than 12 weeks.

9. The medical implant device of claim 6, wherein the second resorbable implant component is wrapped around the first resorbable implant component.

10. The medical implant device of claim 6, wherein the weight ratio of tricalcium phosphate to hydroxyapatite is about 95:5.

11. A medical implant device, comprising:
an implant structure including a first resorbable implant component combined with a second resorbable implant component, the first resorbable implant component comprising a scaffold material comprising ceramic particles, which comprise a weight ratio of tricalcium phosphate to hydroxyapatite of 50:50 to about 95:5, the first resorbable implant component comprising a particulate mineral to resorbable porous matrix weight ratio of at least about 10:1, wherein the ceramic particles resorb more slowly than the second resorbable implant component so that, after implantation of the device in a patient, the second resorbable implant component is resorbed in vivo and the second resorbable implant component comprises a polymer sponge carrier, bone morphogenic protein, and no ceramic particles.

12. The medical implant device of claim 11, wherein the second resorbable implant component is wrapped around the first resorbable implant component.

13. The medical implant device of claim 11, wherein the weight ratio of tricalcium phosphate to hydroxyapatite is about 95:5.

14. A device for tissue repair or replacement,
   comprising first and second components having differing relative rates of in vivo degradation, the second component comprising a polymer sponge carrier, an osteogenic protein and no ceramic particles and having a higher rate of in vivo degradation than the first component, the first and second components being arranged relative to each other so that, after implantation of the device, the second component degrades in vivo and the first component comprises ceramic particles, which comprise tricalcium phosphate and hydroxyapatite in a weight ratio of tricalcium phosphate to hydroxyapatite of about 50:50 to about 95:5 and comprising a particulate mineral to resorbable porous matrix weight ratio of at least about 10:1.

15. The device of claim 14, wherein the second resorbable implant component is wrapped around the first resorbable implant component.

16. The device of claim 14, wherein the weight ratio of tricalcium phosphate to hydroxyapatite is about 95:5.

\* \* \* \* \*